United States Patent
Casara et al.

(12)

(10) Patent No.: US 6,605,604 B1
(45) Date of Patent: Aug. 12, 2003

(54) CARBOXYLIC AND HYDROXAMIC ACID COMPOUNDS INHIBITING METALLOPROTEASES, METHOD FOR PREPARING SAME AND PHARMACEUTICAL COMPOSITIONS CONTAINING THEM

(75) Inventors: Patrick Casara, Villennes sur Seine (FR); Anne Marie Chollet, Le Pecq (FR); Thierry Le Diguarher, Rueil Malmaison (FR); Ghanem Atassi, Saint Cloud (FR); Jacqueline Bonnet, Paris (FR); Alain Pierre, Les Alluets le Roi (FR); Massimo Sabatini, Garches (FR); Gordon Tucker, Paris (FR); Nicolas Guilbaud, La Celle Saint Cloud (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/720,850

(22) PCT Filed: Jun. 29, 1999

(86) PCT No.: PCT/FR99/01556
§ 371 (c)(1),
(2), (4) Date: Dec. 26, 2000

(87) PCT Pub. No.: WO00/00473
PCT Pub. Date: Jan. 6, 2000

(30) Foreign Application Priority Data

Jun. 30, 1998 (FR) .............................. 98 08301

(51) Int. Cl.$^7$ .................... C07D 209/48; C07D 239/96; A61K 31/40; A61P 19/02; A61P 35/04
(52) U.S. Cl. ....................... 514/173; 514/359; 514/367; 514/412; 548/152; 548/207; 548/255; 548/259; 548/452
(58) Field of Search ................. 548/152, 207, 548/255, 259, 452; 514/173, 367, 309, 412

(56) References Cited

U.S. PATENT DOCUMENTS

| 5,646,167 A | 7/1997 | MacPherson et al. ....... 546/175 |
| 5,703,092 A | 12/1997 | Xue et al. ................... 514/303 |

FOREIGN PATENT DOCUMENTS

| EP | 0 574 758 | 12/1993 |
| EP | 0 684 240 | 11/1995 |
| EP | 0 818 442 | 1/1998 |
| WO | 95 19961 | 7/1995 |
| WO | 96 15096 | 5/1996 |
| WO | 96 33176 | 10/1996 |
| WO | 97 18188 | 5/1997 |
| WO | 97 20824 | 6/1997 |
| WO | 97 24117 | 7/1997 |
| WO | 98 05635 | 2/1998 |
| WO | 98 22436 | 5/1998 |

OTHER PUBLICATIONS

J Natl Cancer Inst, Nov. 1976, vol. 57, No. 5, pp. 1199–1202.
Journal of the National Cancer Institute, Feb. 16, 1994, vol. 86, No. 4, Reports pp. 299–304.
Organic Reactions, 1992, vol. 42, Chapter 2, The Mitsunobu Reaction by David L. Hughes, pp 335, 354, and Bibliography page.
J. Org. Chem., 1984, 49 pp 4487–4494.

Primary Examiner—Richard L. Raymond
Assistant Examiner—Venkataraman Balasubramanian
(74) Attorney, Agent, or Firm—The Firm of Hueschen and Sage

(57) ABSTRACT

The invention concerns a compound of formula (I) wherein: n is equal to 0 or 1; $R_1$, $R_2$, $R_3$, $R_4$ represent a hydrogen or an alkyl group, or $R_1$ and $R_3$ together form a cycloalkyl group; $R_5$ represents a hydrogen, an alkyl, cycloalkyl, cycloalkylalkyl, aryl, arylalkyl, heteroaryl, hetereoalkylalkyl, hetereocycloalkyl, hetereocycloalkylalkyl group (all optionally substituted), or a —CO—$R_6$ group; and $R_6$ represents $R_7$ or $OR_7$ or $NR_7R_8$, with $R_7$ representing an aryl, arylalkyl, heteroaryl or heteroarylalkyl, heterocycloalkyl, heterocycloalkylalkyl group (all optionally substituted), and $R_8$ representing an alkyl, aryl, arylalkyl, heteroaryl or heteroarylalkyl (all optionally substituted); or $R_5$ and $R_6$ form with the nitrogen atom and the Z group bearing them a saturated monocyclic, bicyclic or tricyclic group, partially unsaturated or unsaturated, with 5 to 16 chain links containing 1 to 7 heteroatoms and optionally substituted; $R_{10}$ represents a hydrogen atom or a hydroxy group, and in the latter case $R_1$, $R_2$, $R_3$, $R_4$ are independently selected among hydrogen and alkyl; Z represents a hydroxy, alkoxy, alkenyloxy, benzyloxy group or a NH—OR group; X represents a sulphur, a SO, $SO_2$ group (in those cases where $R_3$ and $R_4$ are different from an alkyl) or a group —CO—O— (in which case $R_1$ and $R_3$ form a cycloalkyl group), or X represents an oxygen atom; W represents a $W_1$—(A)$_p$ or $W_1$—B—$W_2$—(A)$_p$ group wherein $W_1$ and $W_2$ represent an aryl or heteroaryl group, A is a standard substituent of aromatic cycles, B a bond, an oxygen or an alkylene, alkenylene, alkynylene group, and p is an integer ranging between 0 and 5; $T_1$ and $T_2$ represent a bond or an alkylene, alkenylene, or alkynylene group. The invention is useful for preparing medicines.

(I)

$$R_6-Z-N(O)_n-T_1-\overset{R_1}{\underset{R_5}{C}}-\overset{R_{10}}{\underset{\underset{O}{\parallel}{C}-Y}{C}}-\overset{R_3}{\underset{}{C}}-X-T_2-W$$

17 Claims, No Drawings

CARBOXYLIC AND HYDROXAMIC ACID COMPOUNDS INHIBITING METALLOPROTEASES, METHOD FOR PREPARING SAME AND PHARMACEUTICAL COMPOSITIONS CONTAINING THEM

BACKGROUND OF THE INVENTION

In the physiological state, the synthesis of connective tissue is in dynamic equilibrium with the degradation of the extracellular matrix. That degradation is due to zinc proteases (metalloproteases) secreted by the cells of the existing matrix: those proteases are, without implying any limitation, collagenases (MMP-1, MMP-8, MMP-13) or gelatinases (MMP-2, MMP-9), Matrilysin (MMP-7) and stromelysins (MMP-3, MMP-10, MMP-11).

In the normal state, those catabolic enzymes are regulated in their synthesis and in their secretion as well as in their extracellular enzymatic activity by natural inhibitors, such as $\alpha_2$-macroglobulin or TIMPs (Tissue Inhibitors of MetalloProteinase), which form inactive complexes with the metalloproteases.

A factor common to the pathologies in which those enzymes are implicated is an imbalance between the activity of the activated enzymes and the activity of their natural inhibitors, the consequence of which is excessive tissue degradation.

Uncontrolled and accelerated degradation of tissue by way of resorption of the extracellular matrix catalysed by the metalloproteases is a parameter common to a number of pathological conditions, such as rheumatoid arthritis, arthrosis, tumour invasion and growth, including malignant dissemination and the formation of metastases, ulceration, atherosclerosis, etc.

More recently, it has been demonstrated that each of those pathologies may be associated with the dominant activity of one or more metalloproteases. Thus, experiments carried out on the Wistar rat have shown a relationship between the development of osteoarthritis and an increase in the production of stromelysin (MMP-3) (Pathol. Res. Pract. 1998, 194, 41). On the other hand, it has been possible to correlate the appearance of rheumatoid arthritis with an increased expression of certain collagenases (MMP-8), which are responsible, alongside polymorphonuclear neutrophils, for cartilage degradation (J. Biol. Chem., 1997, 272, 31504). As for the gelatinases, they seem to play a significant role in tumour invasion. Indeed elevated levels of those enzymes have been demonstrated, in vivo, in several types of tumour, and an activation phenomenon in cancer cells confers invasive properties to non-metastatic tissues (J. of Immunology, 1998, 160, 2967).

Recently, BB94, a metalloprotease inhibitor, has exhibited anti-tumour activity in clinical use, where it has proved to be active in ovarian cancers (Becket et al., DDT 1996, 1, 16).

It may therefore be expected that a metalloprotease inhibitor will restore the equilibrium between protease and inhibitor and, as a result, favourably modify the development of those pathologies. Selectivity in respect of one of the different types of enzyme would allow the efficacy of such a compound to be increased.

Metalloprotease inhibitors are also capable of inhibiting the release of TNF-$\alpha$ (Tumour Necrosis Factor-$\alpha$) from cells. TNF-$\alpha$ is a powerful inflammation mediator implicated in numerous inflammatory pathologies, such as rheumatoid arthritis, asthma etc.

The concept of compounds capable of opposing the release of TNF-$\alpha$ is hence of interest especially in the treatment of the pathologies mentioned above.

DESCRIPTION OF THE PRIOR ART

A certain number of metalloprotease inhibitors have been described in the literature, especially the compounds described in Patent Specifications WO 97/24117, WO 96/35711 and EP 803 505.

The compounds of the present invention are not only new but have also proved to be more powerful inhibitors of metalloproteases and/or of TNF-$\alpha$ release than the inhibitors described in the literature, thus making them potentially useful in the treatment of cancers, rheumatic diseases, such as arthrosis and rheumatoid arthritis, ulcers, atherosclerosis, asthma etc.

DETAILED DESCRIPTION OF THE INVENTION

The present invention relates to the compounds of formula (I):

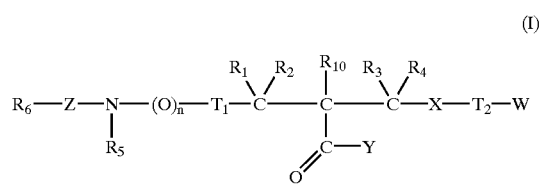

wherein:

n is 0 or 1, $R_1$, $R_2$, $R_3$ and $R_4$ independently represent a hydrogen atom or an alkyl group, or $R_1$ and $R_3$ form together with the carbon atoms carrying them a $(C_5$–$C_8)$cycloalkyl group and in that case $R_2$ and $R_4$ each represents a hydrogen atom, $R_5$ represents a hydrogen atom, an alkyl, $(C_3$–$C_8)$ cycloalkyl, cycloalkyl-$(C_3$–$C_8)$alkyl, optionally substituted aryl, optionally substituted arylalkyl, optionally substituted heteroaryl, optionally substituted heteroarylalkyl, optionally substituted heterocycloalkyl or optionally substituted heterocycloalkylalkyl group, or a —CO—$R_6$ group, $R_6$ represents a group $R_7$, $OR_7$ or $NR_7R_8$ wherein $R_7$ represents an optionally substituted aryl, optionally substituted arylalkyl, optionally substituted heteroaryl or optionally substituted heteroarylalkyl group, and $R_8$ represents an alkyl, optionally substituted aryl, optionally substituted arylalkyl, optionally substituted heteroaryl, optionally substituted heteroarylalkyl, optionally substituted heterocycloalkyl or optionally substituted heterocycloalkylalkyl group, or, $R_5$ and $R_6$ form together with the nitrogen atom and the group Z carrying them a saturated, partially unsaturated or unsaturated mono-, bi- or tri-cyclic group having from 5 to 16 ring members and containing from 1 to 7 hetero atoms selected from nitrogen, oxygen and sulphur and/or a sulphoxide or sulphone group, the said cyclic group being optionally substituted by from 1 to 7 identical or different substituents selected from halogen, alkyl, amino, hydroxy, alkoxy, nitro, mercapto, alkylthio, cyano, oxo, imino, thioxo, carboxy, alkoxycarbonyl and aminocarbonyl (optionally substituted on the nitrogen atom by one or two alkyl groups), $R_{10}$ represents a hydrogen atom or a hydroxy group, and in the latter case $R_1$, $R_2$, $R_3$ and $R_4$ are independently selected from hydrogen and alkyl, Z represents a —CO— group or a —SO$_2$— group, Y represents a hydroxy, alkoxy, alkenyloxy or benzyloxy group or an —NH—OR group wherein R represents a hydrogen atom or an alkyl, alkenyl or benzyl group, X represents: a sulphur atom or a —SO— or —SO$_2$— group and in those cases $R_3$ and $R_4$ are other than an alkyl group, or X represents a —COO— group and in that case $R_1$ and $R_3$ together form a $(C_5-C_8)$cycloalkyl group, or X represents an oxygen atom, W represents a $W_1-(A)_p$ group or a $W_1-B-W_2-(A)_p$ group wherein $W_1$ and $W_2$ independently represent an aryl or heteroaryl group, A, a substituent of the aromatic cyclic group, is attached at any of the positions of that cyclic group and represents a halogen atom or an alkyl, alkoxy, hydroxy, mercapto, cyano, amino, nitro, cyanoalkyl or thioalkyl group, B represents a bond, an oxygen atom or an alkylene, alkenylene or alkynylene group (wherein any one of the carbon atoms of the alkylene, alkenylene or alkynylene groups may be replaced by an oxygen atom), and p represents an integer of from 0 to 5 inclusive, $T_1$ and $T_2$ independently represent a bond or an alkylene, alkenylene or alkynylene group, wherein when $T_2$ represents a bond and n is 0 and at the same time $R_1$, $R_2$, $R_3$ and $R_4$ each represents a hydrogen atom, then $R_5$ and $R_6$ form together with the nitrogen atom and the group Z carrying them a bicyclic group as defined hereinbefore that is other than a 1,3-dioxo-2,3-dihydro-1H-2-isoindolyl group, a 2,5-pyrrolidinedione group or an optionally substituted 2,5-dioxo-1-imidazolinyl group, to their enantiomers, diastereoisomers, and also addition salts thereof with a pharmaceutically acceptable acid or base.

In the compounds of formula (I)

the term "alkyl" denotes a linear or branched hydrocarbon chain having from 1 to 6 carbon atoms, the term "alkenyl" denotes a linear or branched hydrocarbon chain having from 1 to 6 carbon atoms and containing from 1 to 3 double bonds, the term "alkylene" denotes a linear or branched divalent hydrocarbon radical having from 1 to 6 carbon atoms, the term "alkenylene" denotes a linear or branched divalent hydrocarbon radical having from 1 to 6 carbon atoms and containing from 1 to 3 double bonds, the term "alkynylene" denotes a linear or branched divalent hydrocarbon radical having from 1 to 6 carbon atoms and containing from 1 to 3 triple bonds, the term "alkoxy" denotes a linear or branched alkoxy group having from 1 to 6 carbon atoms, the term "aryl" denotes a phenyl or naphthyl group, the term "heteroaryl" denotes an aromatic or partially aromatic mono- or bi-cyclic group having from 5 to 11 ring members and containing from 1 to 4 hetero atoms selected from nitrogen, oxygen and sulphur, for example a furyl, pyridyl, thienyl, indolyl, quinolyl . . . group, the term "heterocycloalkyl" denotes a mono- or bi-cyclic group having from 5 to 11 ring members and containing from 1 to 4 hetero atoms selected from nitrogen, oxygen and sulphur, it being possible for that group to contain one or more unsaturations without being of aromatic character, the expression "optionally substituted" applied to the terms aryl, arylalkyl, heteroaryl, heteroarylalkyl, heterocycloalkyl and heterocycloalkylalkyl denotes that the cyclic moiety of those groups may be substituted by one or more halogen atoms or alkyl, alkoxy, hydroxy, mercapto, cyano, amino, nitro, cyanoalkyl, thioalkyl, aryloxy or arylalkoxy groups.

Among the pharmaceutically acceptable acids there may be mentioned hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid maleic acid, citric acid, ascorbic acid, methanesulphonic acid, camphoric acid etc.

Among the pharmaceutically acceptable bases there may be mentioned sodium hydroxide, potassium hydroxide, triethylamine, tert-butylamine etc.

Preferred compounds of the invention are those wherein $R_{10}$ represents a hydrogen atom.

Other preferred compounds of the invention are those wherein $R_{10}$ represents a hydroxy group.

Advantageously, in the compounds of formula (I), X represents an oxygen or sulphur atom or a —SO$_2$— group.

Preferably, in the compounds of formula (I), $R_2$ and $R_4$ represent a hydrogen atom.

Preferred compounds of the invention are those wherein n is 0.

Other preferred compounds of the invention are those wherein n is 1.

Other preferred compounds of the invention are those wherein $R_1$ and $R_3$ form together with the carbon atoms carrying them a $(C_5-C_8)$cycloalkyl group and $R_2$ and $R_4$ each represents a hydrogen atom. More especially, $R_1$ and $R_3$ form a cyclopentane.

Other preferred compounds of the invention are those wherein $R_2$ and $R_3$ represent a hydrogen atom and $R_1$ and $R_3$ independently represent a hydrogen atom or an alkyl group.

Preferably, in the compounds of formula (I) $R_5$ and $R_6$ form with the nitrogen atom and the group Z carrying them a saturated, partially unsaturated or unsaturated mono- bi- or tri-cyclic group having from 5 to 16 ring members and containing from 1 to 7 hetero atoms selected from nitrogen, oxygen and sulphur and/or a sulphoxide or sulphone group, the said cyclic group being optionally substituted by from 1 to 7 identical or different substituents selected from halogen, alkyl, amino, hydroxy, mercapto, alkoxy, nitro, cyano, oxo, imino and thioxo. Among the substituents there may advantageously be mentioned the groups oxo, amino and alkyl, substituents of the oxo type numbering more especially 1 or 2. Specifically, there may be mentioned the groups 1,3-dioxo-2,3-dihydro-1H-2-isoindolyl, 4-amino-1,3-dioxo-2,3-dihydro-1H-2-isoindolyl, 5-amino -1,3-dioxo-2,3-dihydro -1H-2-isoindolyl, 1-oxo-2,3-dihydro-1H-2-isoindolyl, 2,4-dioxo-3,4-dihydro-2H-1,3-benzoxazin-3-yl, 5,5-dimethyl-2,4-dioxo-1,3-oxazolan-3-yl, 4,4-dimethyl-2,5-dioxo-1-imidazolidinyl, 2,4-dioxo-1,3-thiazolan-3-yl, 3,4,4-trimethyl-2,5-dioxo-1-imidazolidinyl, 1H-benzo[f] isoindole-1,3(2H)-dione, 1H-benzo[d,e]isoquinoline-1,3 (2H)-dione, 5H-dibenzo[c,e]azepine-5,7(6H)-dione and, especially advantageously, the groups 1,3-dioxo-2,3-dihydro-1H-pyrrolo[3,4-c]pyridin-2-yl, 1,1,3-trioxo-2,3-dihydro-1H -1λ6-benzo[d]isothiazol-2-yl, 1-oxo-1,2-dihydro-2-phthalazinyl, 4-oxo-3,4-dihydro-1,2,3-benzotriazin-3-yl and 2,4-dioxo-1,2,3,4-tetrahydro-3-quinazolinyl.

In the compounds of formula (I), $T_1$ and $T_2$ are preferably independently selected from a bond and an alkyl group, $T_1$ being more especially an alkyl group (for example methyl or ethyl).

Preferably, in the compounds of formula (I) Y represents a hydroxy group or an —NH—OR group, R preferably being a hydrogen atom.

Preferred groups W of the invention are the groups $W_1$—(A)$_p$ and $W_1$—B—$W_2$—(A)$_p$ wherein p is 1 and B represents a bond, $W_1$ preferably being an aryl group and A advantageously being selected from halogen, alkoxy and cyano. The preferred aryl group of the invention is the phenyl group.

Among the heteroaryl groups there are mentioned more specifically the groups pyridyl, thienyl, pyrimidyl, pyrazinyl, pyrimidinyl, . . .

A very advantageous aspect of the invention concerns the compounds of formula (I) wherein $R_2$, $R_4$ and $R_{10}$ each represents a hydrogen atom, n is 0, $T_1$ and $T_2$ are independently selected from a bond and an alkylene group, W represents a $W_1$—(A)$_p$ group or a $W_1$—B—$W_2$—(A)$_p$ group wherein p is 1 and B represents a bond, $R_5$ and $R_6$ form together with the nitrogen atom and the group Z carrying them a saturated, partially unsaturated or unsaturated mono- or bi-cyclic group containing from 1 to 5 hetero atoms selected from nitrogen, oxygen and sulphur and/or a sulphoxide or sulphone group, the said cyclic group being optionally substituted by from 1 to 7 identical or different substituents selected from halogen, alkyl, amino, hydroxy, alkoxy, nitro, cyano, oxo, imino and thioxo, and Y represents a hydroxy group or an —NH—OH group.

Among the latter there may be mentioned, more specifically, on the one hand those in which $R_1$ and $R_3$ form together with the carbon atoms carrying them a ($C_5$-$C_8$) cycloalkyl group, and on the other hand those wherein $R_1$ and $R_3$ each represents a hydrogen atom.

Among the preferred compounds of the invention there may be mentioned, more especially, the following compounds:

2-[(4-biphenyl)oxymethyl]-4-(4-oxo-3,4-dihydro-1,2,3-benzotriazin-3-yl)butyric acid (1R,2S,5R)- and (1S,2R,5S)-2-[(4'-chloro-4-biphenyl) sulphanyl]-5-[(4-oxo-3,4-dihydro-1,2,3-benzotriazin-3-yl)methyl]-1-cyclopentanecarboxylic acid 1R,2S,5R)- and (1S,2R,5S)-2-[2-(4'-fluoro-4-biphenyl) ethylsulphanyl]-5-[(1,3-dioxo-2,3-dihydro-1H-2-isoindolyl)methyl]-1-cyclopentanecarboxylic acid 2-[(4-biphenyl)oxymethyl]-4-(1,1,3-trioxo-2,3-dihydro-1H-1λ6-benzo[d]isothiazol-2-yl)butyric acid 2-[(4'-chloro-4-biphenyl)oxymethyl]-4-(4-oxo-3,4-dihydro-1,2,3-benzotriazin-3-yl)butyric acid 2-[(4'-cyano-4-biphenyl)oxymethyl]-4-(4-oxo-3,4-dihydro-1,2,3-benzotriazin-3-yl)butyric acid 2-[(4'-chloro-4-biphenyl)sulphanylmethyl]-4-(4-oxo-3,4-dihydro-1,2,3-benzotriazin-3-yl)butyric acid 2-{[2-(4'-chloro-4-biphenyl)ethyl]sulphanylmethyl}-4-(4-oxo-3,4-dihydro-1,2,3-benzotriazin-3-yl)butyric acid (1R,2S,5R)- and (1S,2R,5S)-2-[2-(4-bromophenyl) ethylsulphanyl]-5-[(1,3-dioxo-2,3-dihydro-1H-2-isoindolyl)methyl]-1-cyclopentanecarboxylic acid (1R,2S,5R)- and (1S,2R,5S)-2-[2-(4'-chloro-4-biphenyl) ethylsulphanyl]-5-[(1,3-dioxo-2,3-dihydro-1H-2-isoindolyl)methyl]-1-cyclopentanecarboxylic acid 2-[2-(4'-chloro-4-biphenyl)ethoxymethyl]-4-(4-oxo-3,4-dihydro-1,2,3-benzotriazin-3yl)butyric acid 2-[(4-biphenyl)oxymethyl]-N-hydroxy-4-(4-oxo-3,4-dihydro-1,2,3-benzotriazin-3-yl)butyramide (1R,2S,5R)- and (1S,2R,5S)-2-[(4'-chloro-4-biphenyl) sulphanyl]-N-hydroxy-5-[(4-oxo-3,4-dihydro -1,2,3-benzotriazin-3-yl)methyl]-1-cyclopentanecarboxamide 2-[(4-biphenyl)oxymethyl]-N-hydroxy-4-(1,1,3-trioxo-2,3-dihydro-1H-1λ6-benzo[d]isothiazol-2-yl)butyramide 2-[(4'-chloro-4-biphenyl)oxymethyl]-N-hydroxy-4-(4-oxo-3,4-dihydro-1,2,3-benzotriazin-3-yl)butyramide 2-[(4'-cyano-4-biphenyl)oxymethyl]-N-hydroxy-4-(4-oxo-3,4-dihydro-1,2,3-benzotriazin-3-yl)butyramide 2-[(4'-chloro-4-biphenyl)sulphanylmethyl]-N-hydroxy-4-(4-oxo-3,4-dihydro-1,2,3-benzotriazin-3-yl)butyramide 2-{[2-(4'-chloro-4-biphenyl)ethyl]sulphanylmethyl}-N-hydroxy-4-(4-oxo-3,4-dihydro-1,2,3-benzotriazin-3-yl) butyramide 2-[2-(4'-chloro-4-biphenyl)ethoxymethyl]-N-hydroxy-4-(4-oxo-3,4-dihydro-1,2,3-benzotriazin-3-yl)butyric.

The present invention relates also to a process for the preparation of the compounds of formula (I).

The process for the preparation of the compounds of formula (I) wherein $R_{10}$ represents a hydrogen atom and X represents a sulphur atom or a —SO— or —$SO_2$— group is characterised in that there is used as starting material a compound of formula (II/a)

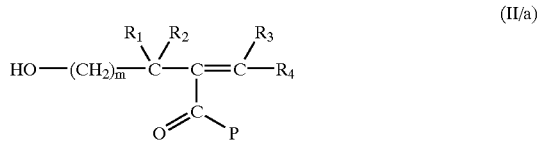

wherein $R_1$, $R_2$, $R_3$ and $R_4$ are as defined for formula (I), P represents an alkoxy, alkenyloxy or benzyloxy group and m is an integer 0 or 1, which may be subjected to a sequence of reactions conventional in organic chemistry, for the purpose of homologising the carbon chain carrying the hydroxy function, to yield a compound of formula (II/b):

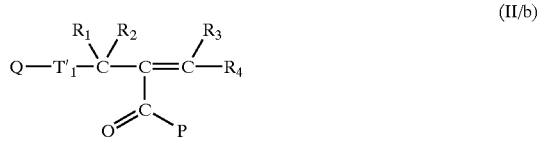

wherein $R_1$, $R_2$, $R_3$, $R_4$ and P are as defined hereinbefore, $T_1'$, which is other than a bond or a methylene group, has the same meanings as $T_1$ in formula (I), and Q represents a hydroxy group or an amino group according to the homologisation sequence used, the compounds of formulae (II/a) and (II/b) constituting the totality of the compounds of formula (II):

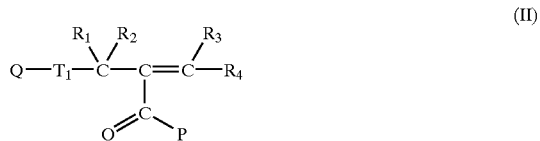

wherein $R_1$, $R_2$, $R_3$, $R_4$, Q and P are as defined hereinbefore and $T_1$ has the same meanings as for formula (I), which compounds are subjected, in basic medium, to the action of a compound of formula (III):

wherein $T_2$, $W_1$, A and p are as defined for formula (I), to yield a compound of formula (IV/a):

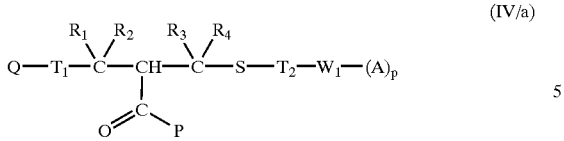
(IV/a)

wherein $R_1, R_2, R_3, R_4, T_1, T_2, W_1, A$, p and P are as defined hereinbefore, which, when one of the substituents A represents a halogen atom, may be treated

- with bis(tributyltin), in the presence of a palladium catalyst, to yield the corresponding stannyl compound, which is subjected under the same conditions to the action of a halogen compound Hal-$W_2$—$(A)_p$ wherein $W_2$, A and p are as defined for formula (I) and Hal represents a halogen atom,
- or with an organometal compound such as a vinyl compound, a tin compound or a boronic acid compound, in the presence or absence of a palladium catalyst, to yield a compound of formula (IV/b):

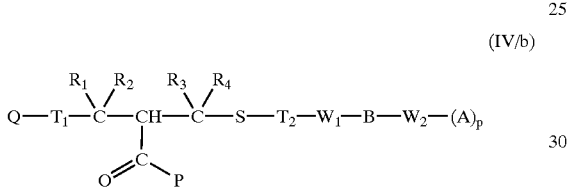
(IV/b)

wherein $R_1, R_2, R_3, R_4, T_1, T_2, W_1, A$, p, P and Q are as defined hereinbefore and B and $W_2$ are as defined for formula (I), the compounds of formulae (IV/a) and (IV/b) constituting the totality of the compounds of formula (IV):

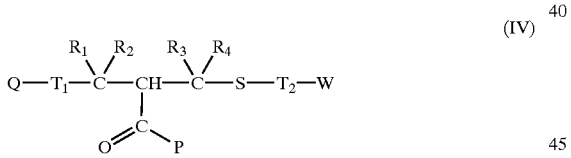
(IV)

wherein $R_1, R_2, R_3, T_1, T_2, Q$, P and W are as defined hereinbefore, which compounds of formula (IV) are subjected:

either, when Q represents a hydroxy group, to a Mitsunobu-type reaction using as reagent a compound of formula (V):

(V)

wherein $R_5, R_6$, Z and n are as defined for formula (I), or, after conversion of hydroxy into a leaving group, to the action, in basic medium, of a salt of the compound of formula (V) as defined hereinbefore, or, when Q represents an amino group, to the action, in basic medium, of a compound of formula (VI):

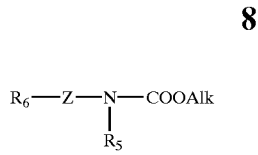
(VI)

wherein $R_5, R_6$ and Z are as defined for formula (I) and Alk represents a linear or branched $(C_1-C_6)$alkyl group, to yield a compound of formula (I/a):

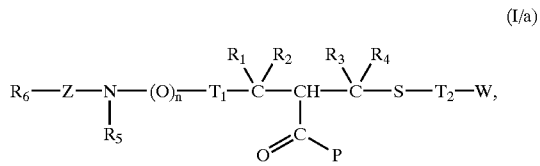
(I/a)

a particular case of the compounds of formula (I) wherein $R_1, R_2, R_3, R_4, R_5, R_6, T_1, T_2$, W, Z, P and n are as defined hereinbefore, the ester function of which may be hydrolysed in acid or basic medium to yield a compound of formula (I/b):

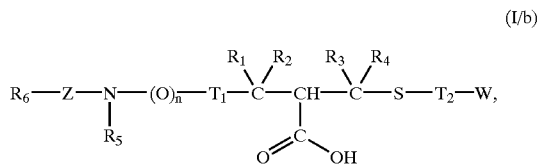
(I/b)

a particular case of the compounds of formula (I) wherein $R_1, R_2, R_3, R_4, R_5, R_6, T_1, T_2$, W, Z and n are as defined hereinbefore, the carboxylic acid function of which may be converted into hydroxamate or into hydroxamic acid to yield a compound of formula (I/c):

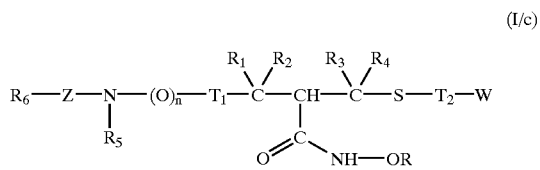
(I/c)

wherein $R_1, R_2, R_3, R_4, R_5, R_6$, T1, $T_2$, W, Z and n are as defined hereinbefore and R has the same meanings as for formula (I), which compounds of formulae (I/a), (I/b) and (I/c):

are optionally purified according to a conventional purification technique,
are optionally separated into their isomers according to a conventional separation technique,
and are converted, if desired, into addition salts with a pharmaceutically acceptable acid or base,
the sulphur atom of which may be oxidised to sulphone or to sulphoxide by conventional oxidation methods at any point during the synthesis, it being understood that the group P present in the various formulae described hereinbefore must be so chosen as to be resistant to the various reagents used and, with that purpose in mind, may be modified at any point during the synthesis, and that the order of the reactions used in the above process may be modified with the aim of simplifying the process or if there is incompatibility between certain reactions and the substituents present in the molecule.

The process for the preparation of the compounds of formula (I) wherein $R_{10}$ represents a hydrogen atom and X represents an oxygen atom is characterised in that there is used as starting material a compound of formula (VII/a):

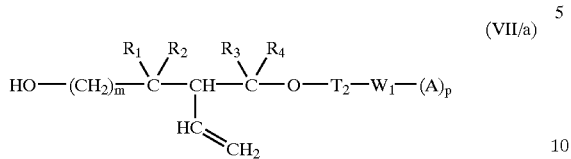

wherein $R_1$, $R_2$, $R_3$, $R_4$, $T_2$, $W_1$, A and p are as defined for formula (I) and m is an integer 0 or 1, which may be subjected to a sequence of reactions conventional in organic chemistry, for the purpose of homologising the carbon chain carrying the hydroxy function, to yield a compound of formula (VII/b):

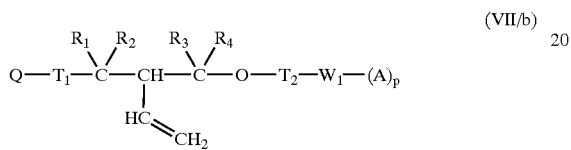

wherein $R_1$, $R_2$, $R_3$, $R_4$, $T_2$, $W_1$, A and p are as defined hereinbefore, $T_1'$, which is other than a bond or a methylene group, has the same meanings as $T_1$ in formula (I), and Q represents a hydroxy group or an amino group according to the homologisation sequence chosen, which compounds of formulae (VII/a) and (VII/b), when one of the substituents A represents a halogen atom, may be treated:
- with bis(tributyltin), in the presence of a palladium catalyst, to yield the corresponding stannyl compound, which is subjected under the same conditions to the action of a halogen compound Hal-$W_2$—(A)$_p$ wherein $W_2$, A and p are as defined for formula (I) and Hal represents a halogen atom,
- or with an organometal compound such as a vinyl compound, a tin compound or a boronic acid compound, in the presence or absence of a palladium catalyst, or in basic medium, to yield a compound of formula (VII/c):

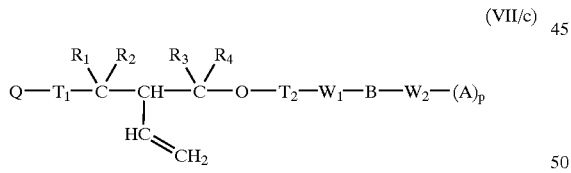

wherein $R_1$, $R_2$, $R_3$, $R_4$, $T_2$, $W_1$, A, p and Q are as defined hereinbefore and $T_1$, B and $W_2$ are as defined for formula (I), the compounds of formulae (VII/a), (VII/b) and (VII/c) constituting the totality of the compounds of formula (VII):

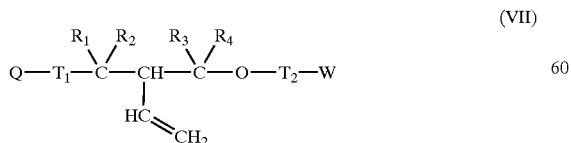

wherein $R_1$, $R_2$, $R_3$, $R_4$, $T_1$, $T_2$ and Q are as defined hereinbefore and W has the same meanings as for formula (I), which compound (VII) is subjected:

either, when Q represents a hydroxy group, to a Mitsunobu-type reaction using as reagent a compound of formula (V):

wherein $R_5$, $R_6$, Z and n are as defined for formula (I), or, after conversion of hydroxy into a leaving group, to the action, in basic medium, of a salt of the compound of formula (V) as defined hereinbefore, or, when Q represents an amino group, to the action of a compound of formula (VI):

wherein $R_5$, $R_6$ and Z are as defined for formula (I) and Alk represents a linear or branched $(C_1-C_6)$alkyl group, to yield a compound of formula (VIII):

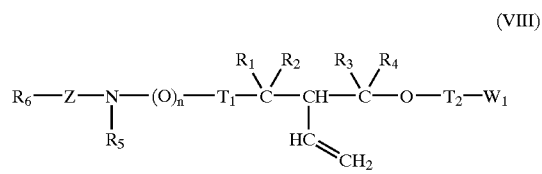

wherein $R_1$, $R_2$, $R_3$, $R_4$, $R_5$, $R_6$, $T_1$, $T_2$, W, Z and n are as defined hereinbefore, which is subjected to an oxidative cleavage reaction to yield a compound of formula (I/d):

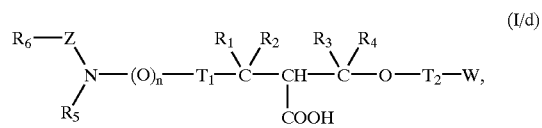

a particular case of the compounds of formula (I) wherein $R_1$, $R_2$, $R_3$, $R_4$, $R_5$, $R_6$, Z, $T_1$, $T_2$, W and n are as defined hereinbefore, and the carboxylic acid function of which may be converted into ester, into hydroxamate or into hydroxamic acid to yield a compound of formula (I/e):

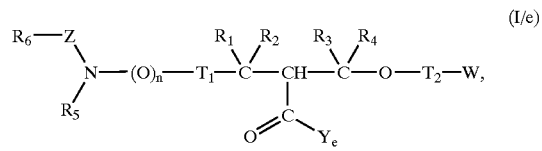

a particular case of the compounds of formula (I) wherein $R_1$, $R_2$, $R_3$, $R_4$, $R_5$, $R_6$, Z, $T_1$, $T_2$, W and n are as defined hereinbefore and $Y_e$, which is other than a hydroxy group, has the same meanings as Y in formula (I), which compounds of formulae (I/d) and (I/e):
are optionally purified according to a conventional purification technique,
are optionally separated into their isomers according to a conventional separation technique, and are converted, if desired, into addition salts with a pharmaceutically acceptable acid or base, it being understood that the oxidative cleavage of the double bond can be carried out at another stage of the process described above, and that the order of the reactions of that process may be modified with the aim of simplifying the process or if there is incompatibility between certain reactions and the substituents present in the molecule.

The process for the preparation of the compounds of formula (I) wherein $R_{10}$ represents a hydrogen atom and X represents a —CO—O— group is characterised in that there is used as starting material a compound of formula (IX):

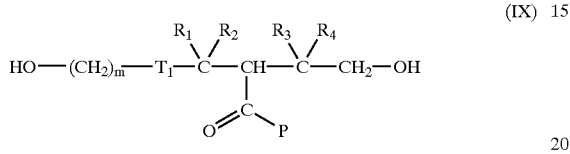

(IX)

wherein $R_1$, $R_2$, $R_3$, $R_4$ are as defined for formula (I), P represents an alkoxy, alkenyloxy or benzyloxy group and m is an integer 0 or 1, which, after protection of one of the two hydroxy functions, is subjected to oxidation in the presence of an appropriate alcohol of formula P'—OH to yield a compound of formula (X/a):

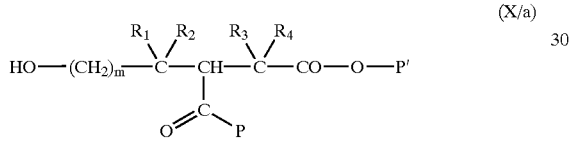

(X/a)

wherein $R_1$, $R_2$, $R_3$, $R_4$, m and P are as defined hereinbefore and P' represents an alkyl, alkenyl or benzyl group (so selected that the two ester functions present are different), which may be subjected to a sequence of reactions conventional in organic chemistry, for the purpose of homologising the carbon chain carrying the hydroxy function, to yield a compound of formula (X/b):

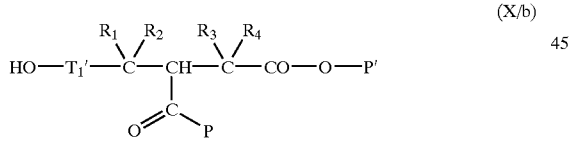

(X/b)

wherein $R_1$, $R_2$, $R_3$, $R_4$, P and P' are as defined hereinbefore and $T_1'$, which is other than a bond or a methylene group, has the same meanings as $T_1$ in formula (I), which compounds (X/a) and (X/b) are subjected:

either to a Mitsunobu-type reaction using as reagent a compound of formula (V):

(V)

wherein $R_5$, $R_6$, Z and n are as defined for formula (I),
or, after conversion of hydroxy into a leaving group, to the action of a salt of the compounds of formula (V) as defined hereinbefore to yield a compound of formula (XI):

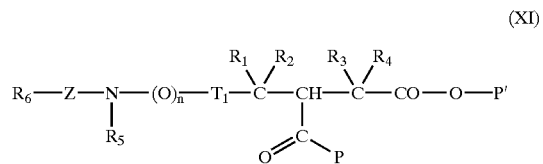

(XI)

wherein $R_1$, $R_2$, $R_3$, $R_4$, $R_5$, $R_6$, P, P' and n are as defined hereinbefore and $T_1$ has the same meanings as for formula (I), which, after selective hydrolysis of one of the two ester functions, is subjected to the action of a compound of formula (XII/a):

HO—$T_2$—W  (XII/a)

wherein $T_2$ and W are as defined for formula (I), to yield a compound of formula (XIII/a):

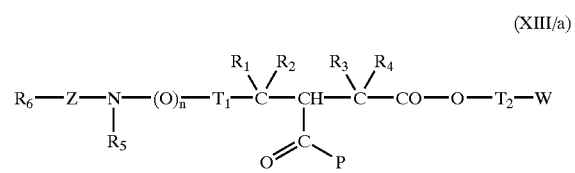

(XIII/a)

wherein $R_1$, $R_2$, $R_3$, $R_4$, $R_5$, $R_6$, $T_1$, $T_2$, W, n and p are as defined hereinbefore, it being possible for the compound of formula (XII/a) to be replaced, when that is advantageous, by a compound of formula (XII/b):

HO—$T_2$—$W_1$—$(A)_p$  (XII/b)

wherein $T_2$, $W_1$, A and p are as defined for formula (I), to yield a compound of formula (XIII/b):

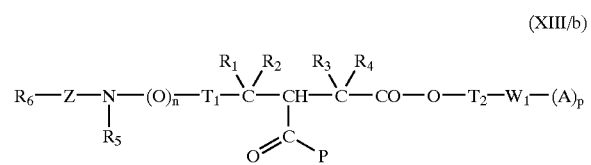

(XIII/b)

wherein $R_1$, $R_2$, $R_3$, $R_4$, $R_5$, $R_6$, $T_1$, $T_2$, $W_1$, A, p, P and n are as defined hereinbefore, which, when one of the substituents A represents a halogen atom, may be treated:

with bis(tributyltin), in the presence of a palladium catalyst, to yield the corresponding stannyl compound, which is subjected under the same conditions to the action of a halogen compound Hal-$W_2$—$(A)_p$ wherein $W_2$, A and p are as defined for formula (I) and Hal represents a halogen atom, or with an organometal compound such as a vinyl compound, a tin compound or a boronic acid compound, in the presence or absence of a palladium catalyst, or in basic medium, to yield a compound of formula (XIII/c):

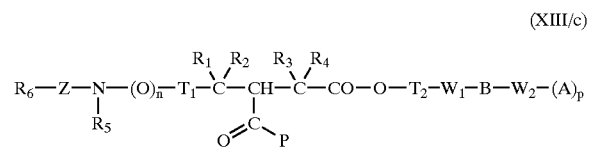

(XIII/c)

wherein $R_1$, $R_2$, $R_3$, $R_4$, $R_5$, $R_6$, $T_1$, $T_2$, $W_1$, A, P and p are as defined hereinbefore, and B and $W_2$ are as defined for formula (I), the compounds of formulae (VIII/a), (VIII/b) and (VIII/c) constituting the totality of the compounds of formula (I/f):

(I/f)

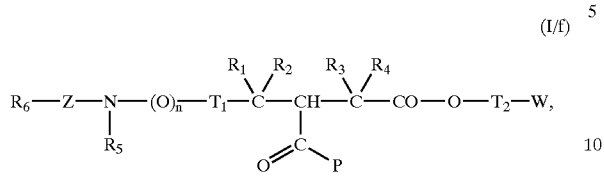

a particular case of the compounds of formula (I) wherein $R_1, R_2, R_3, R_4, R_5, R_6, T_1, T_2, W, P$ and n are as defined hereinbefore, the ester function of which may be selectively converted into carboxylic acid to yield a compound of formula (I/g):

(I/g)

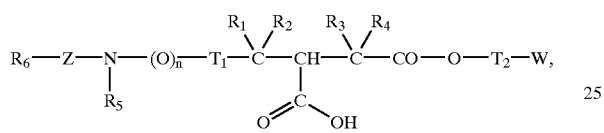

a particular case of the compounds of formula (I) wherein $R_1, R_2, R_3, R_4, R_5, R_6, T_1, T_2, W$ and n are as defined hereinbefore, and the acid function of which may be converted into hydroxamate or into hydroxamic acid to yield a compound of formula (I/h):

(I/h)

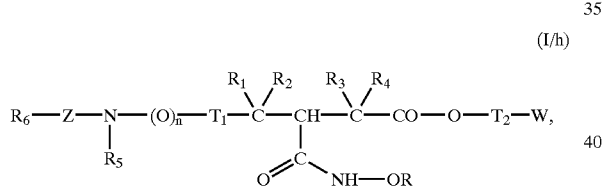

a particular case of the compounds of formula (I) wherein $R_1, R_2, R_3, R_4, R_5, R_6, T_1, T_2, W$ and n are as defined hereinbefore, and R has the same meanings as for formula (I), which compounds of formulae (I/f), (I/g) and (I/h):

are optionally purified according to a conventional purification technique, are optionally separated into their isomers according to a conventional separation technique, and are converted, if desired, into addition salts with a pharmaceutically acceptable acid or base, it being understood that the group P present in the various formulae described hereinbefore must be so chosen as to be resistant to the various reagents used and, with that purpose in mind, may be modified at any point during the synthesis, and that the order of the reactions used in the above process may be modified with the aim of simplifying the process or if there is incompatibility between certain reactions and the substituents present in the molecule.

The process for the preparation of the compounds of formula (I) wherein $R_{10}$ represents a hydroxy group is characterised in that there is used as starting material a compound of formula (XIV/a):

(XIV/a)

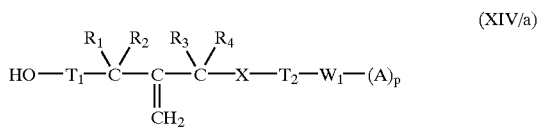

wherein $R_1, R_2, R_3, R_4, T_1, T_2, X, W_1, A$ and p are as defined for formula (I), which, when one of the substituents A represents a halogen atom, may be treated:

with bis(tributyltin), in the presence of a palladium catalyst, to yield the corresponding stannyl compound, which is subjected under the same conditions to the action of a halogen compound Hal-$W_2$—$(A)_p$ wherein $W_2$, A and p are as defined for formula (I) and Hal represents a halogen atom, or with an organometal compound such as a vinyl compound, a tin compound or a boronic acid compound in the presence or absence of a palladium catalyst or in basic medium, to yield a compound of formula (XIV/b):

(XIV/b)

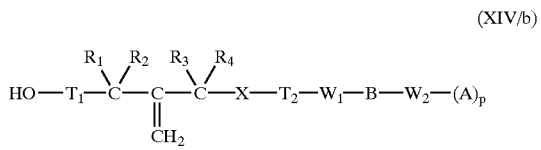

wherein $R_1, R_2, R_3, R_4, T_1, T_2, X, A, B, W_1, W_2$ and p are as defined for formula (I), which compounds (XIV/a) and (XIV/b) are subjected:

either to a Mitsunobu-type reaction using as reagent a compound of formula (V):

(V)

wherein $R_5, R_6, Z$ and n are as defined for formula (I), or, after conversion of hydroxy into a leaving group, to the action of a salt of the compounds of formula (V) as defined hereinbefore, to yield a compound of formula (XV):

(XV)

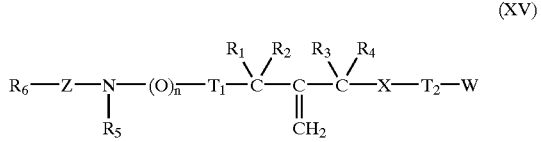

wherein $R_1$, $R_2$, $R_3$, $R_4$, $R_1$, $R_6$, X, Z, W, $T_1$, $T_2$ and n are as defined for formula (I), which is subjected to a dihydroxylation reaction to yield a compound of formula (XVI):

(XVI)

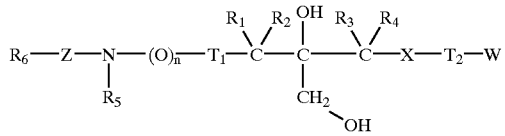

wherein $R_1$, $R_2$, $R_3$, $R_4$, $R_5$, $R_6$, X, Z, W, $T_1$, $T_2$ and n are as defined hereinbefore, the primary alcohol function of which is oxidised, directly or by way of an aldehyde, to yield the corresponding acid of formula (I/i):

(I/i)

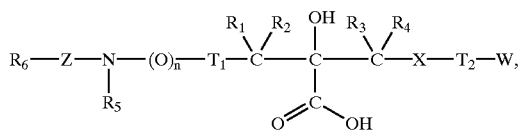

a particular case of the compounds of formula (I) wherein $R_1$, $R_2$, $R_3$, $R_4$, $R_5$, $R_6$, X, Z, W, $T_1$, $T_2$ and n are as defined hereinbefore, the acid function of which compound (I/i) may be converted into hydroxamate, into hydroxamic acid or into ester to yield a compound of formula (I/j):

(I/j)

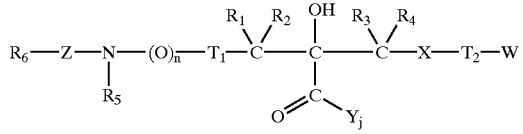

wherein $R_1$, $R_2$, $R_3$, $R_4$, $R_5$, $R_6$, X, Z, W, $T_1$, $T_2$ and n are as defined for formula (I): and $Y_j$, which is other than a hydroxy group, has the same meanings as Y in formula (I), which compounds of formulae (I/i) and (I/j):

are optionally purified according to a conventional purification technique, are optionally separated into their isomers according to a conventional separation technique, and are converted, if desired, into addition salts with a pharmaceutically acceptable acid or base, it being understood that the order of the reactions used in the above process may be modified with the aim of simplifying the process or if there is incompatibility between certain reactions and the substituents present in the molecule.

In the case where, in the compounds of formula (I) it is desired to obtain, $R_1$ and $R_3$ form together with the carbon atoms carrying them a $(C_5-C_8)$cycloalkyl group, the processes described above result in "trans-trans" ($D_{tt}$) and "trans-cis" ($D_{tc}$) diastereoisomers:

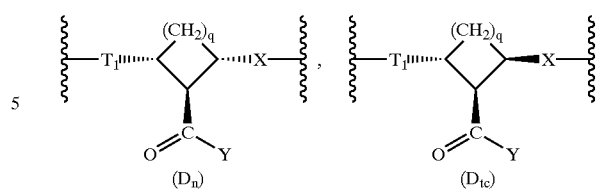

wherein X, Y and $T_1$ are as defined for formula (I) and Q is an integer 2, 3, 4 or 5.

The pairs of diastereoisomers are separated by conventional methods at the opportune moment during the process to yield each of them in racemic form.

Among the conventional homologisation sequences used in the above processes there may be mentioned, for example:

conversion of the hydroxy function into a leaving group or activation of that function by a Mitsunobu-type mechanism, replacement by a cyanide, and reduction of the cyano function to amine or hydroxy, oxidation of the hydroxy function to the aldehyde and increasing the length of the carbon chain by a Wittig or related reaction.

The invention relates also to pharmaceutical compositions comprising as active ingredient at least one compound of formula (I), alone or in combination with one or more inert, non-toxic excipients or carriers.

Among the pharmaceutical compositions according to the invention there may be mentioned more especially those which are suitable for oral, parenteral or nasal administration, tablets or dragées, sublingual tablets, gelatin capsules, lozenges, suppositories, creams, ointments, dermal gels etc.

The useful dosage varies in accordance with the age and weight of the patient, the nature and severity of the disorder and the administration route, which may be nasal, rectal, parenteral or oral. Generally, the unit dosage ranges from 50 mg to 5 g for a treatment of from 1 to 3 administrations per 24 hours.

The following Examples illustrate the invention but do not limit it in any way. The structures of the described compounds were confirmed by conventional spectroscopic techniques.

The preparations described below result in the starting materials used in the synthesis of the compounds of the invention.

PREPARATION A tert-Butyl R,S-5-(hydroxymethyl)-1-cyclopentene-1-carboxylate

A mixture of (26.4 g; 0.204 mol) of 2,5-dimethoxytetrahydrofuran and 200 ml of a 0.5M hydrochloric acid solution is stirred for 2 hours 30 minutes at 80° C. After cooling, the reaction mixture is neutralised with a saturated aqueous solution of $KHCO_3$. An aqueous solution of 0.05 molar equivalents of $K_2CO_3$ (15 ml) and then, dropwise, (dimethoxyphosphoryl)acetic acid tert-butyl ester (40.4 ml; 0.204 mol) are added. Finally, 2 molar equivalents of $K_2CO_3$ (56.39 g; 0.408 mol) in aqueous solution (100 ml) are added. The whole is stirred at ambient temperature for one night. The residue is extracted with ether, and the organic phase is washed with a saturated aqueous solution of sodium chloride until neutral and dried over magnesium sulphate. After filtration, the filtrate is concentrated to yield the expected compound.

PREPARATION B

Benzyl(1R,2R,3S)- and (1S,2S,3R)-2,5-bis-(hydroxymethyl)-1-cyclopentanecarboxylate Step a: Benzyl exo-2-oxobicylo[2.2.1]heptane-7-carboxylate 0.25 mol (48 g) of EDC is added to a solution of 0.23 mol (35 g) of exo-2-oxo-bicylo[2.2.1]heptane-7-carboxylic acid (prepared in accordance with the method described in *Tetrahedron*, 1981, 37, Suppl., 411) in 400 ml of dichloromethane placed at 0° C. When the solution has become homogeneous, 0.25 mol (26 ml) of benzyl alcohol is added dropwise followed by 0.022 mol (2.7 g) of DMPA. The reaction mixture is then stirred for 2 hours at ambient temperature, hydrolysed cold with an aqueous 10% hydrochloric acid solution and extracted with dichloromethane. The organic phase is washed with a saturated aqueous solution of sodium chloride until neutral and dried over magnesium sulphate. After concentration, the expected product is isolated following purification by chromatography on silica gel using an 8:2 heptane/ethyl acetate mixture as eluant.

Step b: Benzyl 2-trifluoromethanesulphonyloxybicyclo[2.2.1]hept-2-ene-7-carboxylate 150 mmol (31 g) of 2,6-di-tert-butyl-4-methylpyridine and then, dropwise, 150 mmol (25.38 ml) of triflic anhydride, are added to a solution of 137 mmol (33.5 g) of the compound obtained in the preceding Step in 1 litre of dichloromethane. After the addition, the reaction mixture is heated at reflux for 18 hours. A saturated aqueous solution of ammonium chloride is then added (200 ml) and the product is extracted several times with ethyl acetate. The organic phase is washed with a saturated aqueous solution of sodium chloride until neutral and dried over magnesium sulphate. The expected product is obtained after removal of the solvent by evaporation, and purification by chromatography on silica gel using a 95:5 heptane/ethyl acetate mixture as eluant.

Step c: Benzyl bicyclo[2.2.1]hept-2-ene-7-carboxylate

There are added in succession to a solution of 0.133 mol (50 g) of the compound obtained in the preceding Step, in 650 ml of anhydrous dimethylformamide, 0.4 mol (95 ml) of tributylamine, 2.65 mmol (2 g) of $Pd(OAc)_2(PPh_3)_2$ and, dropwise, 0.265 mol (10 ml) of formic acid. When the addition is complete, the reaction mixture is heated at 60° C. for 2 hours. After concentration, the residue is taken up in ethyl acetate, washed with a saturated aqueous solution of $NaHCO_3$, and then with a saturated aqueous solution of sodium chloride until neutral, and dried over magnesium sulphate. The expected product is obtained after removal of the solvent by evaporation, and purification by chromatography on silica gel using a 95:5 heptane/ether mixture as eluant.

Step d: Benzyl(1R,2R,3S)- and (1S,2S,3R)-2,5-di-(formyl)-1-cyclopentane-carboxylate A solution, cooled to −78° C., of 0.175 mol (40 g) of the compound obtained in the preceding Step in 700 ml of dichloromethane is treated directly with ozone for 2 hours at that temperature. When the starting material has disappeared completely, the reaction mixture is purged with oxygen and then with nitrogen until the blue colour has completely disappeared, and 0.88 mol (64.3 ml) of dimethyl sulphide is added. The mixture is stirred for 24 hours, while allowing a progressive return to ambient temperature. After concentration, the expected product is isolated and can be used directly in the following Step.

Step e: Benzyl(1R,2R,3S)- and (1S,2S,3R)-2,5-bis-(hydroxymethyl)-1-cyclopentanecarboxylate 1.05 mol (148 ml) of 3-ethyl-3-pentanol is added dropwise to a suspension of 0.35 mol (13.3 g) of lithium aluminium hydride in 450 ml of anhydrous tetrahydrofuran placed under argon, and the whole is heated at gentle reflux for 2 hours. After cooling to ambient temperature, the reaction mixture is transferred into a solution of 0.175 mol (45.5 g) of the compound obtained in the preceding Step in 350 ml of anhydrous tetrahydrofuran that has been placed under argon at −78° C., and stirring of the mixture is continued at that temperature for 4 hours. The reaction mixture is then hydrolysed by adding 1 litre of a 1M hydrochloric acid solution, with stirring, over a period of 1 hour, while allowing a progressive return to ambient temperature. After extraction with ethyl acetate, washing the organic phase with a saturated aqueous solution of sodium chloride until neutral and drying over magnesium sulphate, the aqueous phase is concentrated. The expected product is isolated by purification by chromatography on silica gel using a 75:25 dichloromethane/-ethyl acetate mixture as eluant.

PREPARATION C

3-[(4-Bromophenoxy)methyl]-4-penten-1-ol

Step a: trans-1-Bromo-4-[4-chloro-2-butenyl)oxy]benzene 80 mmol (17.4 g) of caesium carbonate are added to a solution, cooled to 0° C., of 80 mmol (10 g) of trans-1,4-dichloro-2-butene and 53.3 mmol (9.23 g) of para-bromophenol in 500 ml of acetonitrile, and then the mixture is stirred at ambient temperature for 4 days. The mixture is hydrolysed with 250 ml of a saturated aqueous solution of ammonium chloride and then extracted with ethyl acetate. The organic phases are combined and washed with a saturated aqueous solution of sodium chloride and then dried over magnesium sulphate. After evaporation, the expected product is obtained following purification by chromatography on silica gel using a 98:2 petroleum ether/ethyl acetate mixture as eluant.

Step b: 4-(4-Bromophenoxy)-2-butenyl acetate

The compound obtained in the preceding Step (11.5 mmol, 3 g) is dissolved in 150 ml of acetone. After the addition of 13.8 mmol (4.15 g) of tetrabutylammonium acetate, the mixture is heated at reflux for 5 hours. The solvent is evaporated off and then the residue is redissolved in 250 ml of dichloromethane. The solution is washed with water (3×100 ml), dried over magnesium sulphate and concentrated. The oily residue is purified by chromatography on silica gel, using a 97:3 petroleum ether/ethyl acetate mixture as eluant, to yield the expected compound.

Step c: 4-(4-Bromophenoxy)-2-buten-1-ol 54 ml of a 2M aqueous sodium hydroxide solution are added to a solution of 10.9 mmol (3.1 g) of the compound obtained in the preceding Step in 50 ml of methanol. The mixture is stirred at ambient temperature for 16 hours and then neutralised with a 1M aqueous hydrochloric acid solution. The aqueous phase is extracted with dichloromethane (3×100 ml). The organic phases are washed with a saturated aqueous solution of sodium chloride, dried over magnesium sulphate and concentrated. The residue is purified by chromatography on silica gel, using an 8:2 petroleum ether/ethyl acetate mixture as eluant, to yield the expected product.

Step d: Ethyl 3-[(4-bromophenoxy)methyl]-4-pentenoate

A mixture of 61.7 mmol (11.3 ml) of triethyl orthoacetate, 0.05 mmol (4 μl) of propionic acid and 10.3 mmol (2.5 g) of the compound described in the preceding Step is heated at 125° C. for a whole day while distilling off the ethanol formed. The temperature is subsequently brought to 135° C. for 1 night and then triethyl orthoacetate is distilled off in vacuo. The desired product is obtained by purification by chromatography on silica gel using a 98:2 petroleum ether/ethyl acetate mixture as eluant.

Step e: 3-[(4-Bromophenoxy)methyl]-4-penten-1-ol 5.32 mmol (0.2 g) of lithium aluminium hydride suspended in 10 ml of diethyl ether are slowly added to a solution, cooled to −78° C., of 6.64 mmol (2.1 g) of the compound obtained in the preceding Step in 25 ml of anhydrous diethyl ether, and the mixture is then stirred for 24 hours at −78° C. The reaction is hydrolysed with water, the phases are separated, and the aqueous phase is extracted 3 times with 30 ml of diethyl ether each time. The organic phases are combined, washed with a saturated aqueous solution of sodium chloride and dried over magnesium sulphate. Removal of the solvent by evaporation yields the expected product.

PREPARATION D tert-Butyl 4-hydroxy-2-methylenebutyrate

Step a: 2-[2-(Methoxycarbonyl)ethyl]acrylic acid 120 g of Amberlyst-15 resin are added to a solution of itaconic acid, 0.76 mole (100 g), in 1.5 litres of anhydrous methanol. The whole is stirred slowly for 48 hours at ambient temperature. The reaction mixture is then filtered. The methyl monoester is thus obtained by simple concentration of the filtrate.

Step b: Methyl 3-tert-butoxycarbonyl-3-butenoate

To a solution, cooled to 0° C., of methyl monoester (0.18 mol, 26 g) obtained in Step a in 130 ml of anhydrous $CH_2Cl_2$, there is added in the course of 1 hour isobutylene, and then 1.3 ml of concentrated sulphuric acid. The whole, hermetically sealed, is stirred at ambient temperature for 24 hours. The reaction mixture is then neutralised cold with a saturated $NaHCO_3$ solution and subsequently extracted with $CH_2Cl_2$. The organic phase is then washed with a saturated NaCl solution until neutral and subsequently dried over $MgSO_4$. The diester is obtained in the form of a colourless oil by concentrating the solvent to dryness.

Step c: 3-tert-Butoxycarbonyl-3-butenoic acid

A solution of 0.26 mole (10.78 g) of lithium hydroxide in 100 ml of $H_2O$ is added to 0.17 mol (34.3 g) of the diester compound obtained in Step b dissolved in 100 ml of dioxane. The whole is stirred at ambient temperature for 24 hours. 100 ml of $H_2O$ are then added and the aqueous phase is washed twice with 100 ml of $Et_2O$ each time, then acidified with dilute HCl and, finally, extracted with AcOEt. The organic phase is subsequently washed with a saturated NaCl solution and then dried over $MgSO_4$. The product is obtained in the form of a colourless oil by concentrating the solvent to dryness.

Step d: tert-Butyl 4-hydroxy-2-methylenebutyrate

A solution of the compound described in the preceding Step (4.85 mmol, 0.9 g) in 10 ml of THF is added dropwise to a suspension of 5.82 mmol (0.22 g) of $NaBH_4$ in 20 ml of anhydrous THF, and the whole is stirred at ambient temperature for 1 hour. It is brought to 0° C. and then a solution of $I_2$ (2.42 mmol, 0.615 g) in 20 ml of THF is added and the reaction mixture is subsequently stirred at ambient temperature for 24 hours. The mixture is hydrolysed with a saturated ammonium chloride solution and extracted with ethyl acetate. The organic phase is then washed with a saturated sodium chloride solution, dried over magnesium sulphate and concentrated to yield the expected compound.

PREPARATION E

2-(4-Bromophenyl)-1-ethanethiol

Step a: 4-Bromophenethyl thioacetate 5 mmol (1 ml) of DIAD are added to a solution, cooled to 0° C., of 5 mmol (1.32 g) of triphenylphosphine in 16 ml of tetrahydrofuran. After stirring the mixture cold for 15 minutes, there is added dropwise thereto a mixture of 2.5 mmol (0.5 g) of 2-(4-bromophenyl)-1-ethanol and 5 mmol (0.83 ml) of thioacetic acid diluted with 5 ml of tetrahydrofuran. The mixture is stirred cold for a further 10 minutes and then the temperature is brought to ambient temperature for 18 hours. The solvents are evaporated off. The residue is taken up in diisopropyl ether and the precipitate formed is filtered off. The filtrate is concentrated and then purified by chromatography on silica gel. using petroleum ether as eluant, to yield the expected product.

Step b: 2-(4-Bromophenyl)-1-ethanethiol 7.48 mmol (0.284 mg) of lithium aluminium hydride dissolved in 21 ml of diethyl ether are added dropwise to a solution, cooled to 0° C. by an ice bath, of 1.87 mmol (0.48 g) of the compound described in the preceding Step in 13 ml of diethyl ether. After stirring cold for 2 hours, the mixture is hydrolysed with an aqueous N hydrochloric acid solution (13 ml). The mixture is extracted with diethyl ether (twice with 250 ml each time). The ethereal phases are washed with water (twice with 100 ml each time) and then dried over magnesium sulphate before being concentrated. Purification by chromatography on silica gel, using a 95:5 petroleum ether/diethyl ether mixture as eluant, yields the expected product.

PREPARATION F

(4-Bromophenyl)methanethiol

The expected product is obtained in accordance with the procedure described in Preparation E, with the replacement of 2-(4-bromophenyl)-1-ethanol with (4-bromophenyl)methanol in Step a.

PREPARATION G

3-[(4-Bromophenethyl)oxymethyl]-4-penten-1-ol

The expected product is obtained in accordance with the procedure described in Preparation C, with the replacement of para-bromophenol with 2-(4-bromophenyl)ethanol in Step a.

PREPARATION H

4-[(4-Bromophenoxy)methyl]-4-penten-1-ol

The expected product is obtained in accordance with the procedure described in Preparation C, using 3-chloromethyl-3-chloro-1-propene as starting material in Step a.

EXAMPLE 1

(1R,2S,5R)- and (1S,2R,5S)-2-[(4-biphenyl)sulphanyl]-5-[(1,3-dioxo-2,3-dihydro-1H-2-isoindolyl)methyl]-1-cyclopentanecarboxylic acid Step a: tert-Butyl R,S-(5-acetoxy)-1-cyclopentene-1-carboxylate The compound described in Preparation A (37 g; 0.201 mol) is dissolved in 200 ml of dichloromethane at 0° C., 0.603 mol (48.6 ml) of pyridine is added dropwise, followed by 0.402 mol (38 ml;) of acetic anhydride. The whole is then stirred at ambient temperature for one night. The reaction mixture is subsequently concentrated, and the residue is taken up in ethyl acetate, washed with a dilute aqueous 10% hydrochloric acid solution, with a saturated aqueous solution of $NaHCO_3$, and then with a saturated sodium chloride solution. The organic phase is dried over $MgSO_4$ and concentrated. The expected product is obtained by purification by chromatography on silica gel using a 95:5 heptane/ethyl acetate mixture as eluant.

Step b: tert-Butyl R,S-5-(methanesulphinylmethylsulphanylmethyl)-1-cyclopentene-1-carboxylate A 1.6M solution of n-butyllithium in hexane is added to a solution, placed under argon at −78° C., of 532 mmol (6.2 ml) of methanesulphinyl-methyl-sulphanyl-methane in 100 ml of anhydrous tetrahydrofuran, and the whole is stirred at that temperature for 30 minutes. The mixture is transferred into a mixture of the compound obtained in the preceding Step (38 mmol, 8.6 g) and copper iodide (38 mmol, 7.24 g) in 100 ml of anhydrous tetrahydrofuran that has been placed under argon at −78° C. The whole is subsequently stirred at −50° C. for 2 hours, then at −30° C. for 2 hours. When the starting material has disappeared completely, the reaction mixture is hydrolysed with a saturated aqueous solution of ammonium chloride while allowing a progressive return to ambient temperature. The mixture is extracted with ethyl acetate and the organic phase is washed with a saturated aqueous solution of sodium chloride until neutral, dried over $MgSO_4$ and concentrated. The expected product is obtained by purification by chromatography on silica gel using a 4:6 dichloromethane/ethyl acetate mixture as eluant.

Step c: tert-Butyl R,S-5-formyl-1-cyclopentene-1-carboxylate 2 ml of a dilute aqueous 70% $HClO_4$ solution are slowly added to a solution of 125 mmol (3.65 g) of the compound obtained in the preceding Step in 150 ml of diethyl ether at 0° C., and the whole is stirred while maintaining the temperature below 10° C. After 2 hours, the reaction mixture is hydrolysed with a saturated aqueous solution of $NaHCO_3$ while allowing a progressive return to ambient temperature, and then extracted with ethyl acetate. The organic phase is washed with a saturated aqueous solution of sodium chloride until neutral, dried over magnesium sulphate, and concentrated. The expected product is obtained by purification by chromatography on silica gel using a 95:5 heptane/ethyl acetate mixture as eluant.

Step d: tert-Butyl R,S-5-(hydroxymethyl)-1-cyclopentene-1-carboxylate 7.5 mmol (1.06 ml) of 3-ethyl-3-pentanol are added dropwise to a suspension of 2.5 mmol (95 mg) of lithium aluminium hydride in 25 ml of anhydrous tetrahydrofuran under argon and the whole is heated under gentle reflux for 1 hour. After cooling, the solution is transferred into a solution of the compound obtained in the preceding Step (2.09 mmol, 410 mg) in 25 ml of anhydrous tetrahydrofuran under argon and at −78° C. The mixture is stirred at that temperature for 4 hours. The reaction mixture is then hydrolysed with 25 ml of a saturated aqueous solution of ammonium chloride and subsequently extracted several times with ethyl acetate. The organic phase is washed with a saturated aqueous solution of sodium chloride until neutral and dried over magnesium sulphate. The expected product is isolated by concentration and purification of the residue by chromatography on silica gel using a 9:1 petroleum ether/ethyl acetate mixture as eluant.

Step e: tert-Butyl(1R,2S,5R)- and (1S,2R,5S)-2-(4-bromophenylsulphanyl)-5-(hydroxymethyl)-1-cyclopentanecarboxylate 0.75 mmol (0.14 g) of 4-bromothiophenol is added to a solution of 0.5 mmol (0.1 g) of the compound obtained in the preceding Step in 15 ml of piperidine and the whole is heated at reflux for 4 hours. The reaction mixture is then concentrated and taken up in ethyl acetate. The organic phase is washed with an aqueous 10% hydrochloric acid solution, with a saturated aqueous solution of $NaHCO_3$, and then with a saturated aqueous solution of sodium chloride until neutral, dried over magnesium sulphate and concentrated. The expected product is obtained by purification by chromatography on silica gel using an 8:2 heptane/ethyl acetate mixture as eluant.

Step f: tert-Butyl(1R,2S,5R)- and (1S,2R,5S)-2-[(4-biphenyl)sulphanyl]-5-(hydroxymethyl)-1-cyclopentanecarboxylate To a solution of 0.33 mmol (102 mg) of the compound obtained in the preceding Step in 10 ml of toluene, there are added tetrakispalladium (63 mg; 0.054 mmol), and phenylboronic acid (49 mg; 0.4 mmol) dissolved in 10 ml of ethanol, and then 10 ml of a sodium carbonate solution (98 mg; 0.73 mmol). The whole is heated at reflux for 5 hours. The mixture is then cooled and concentrated and subsequently taken up in ethyl acetate. After washing several times with a saturated aqueous solution of sodium chloride until neutral, the organic phase is dried over magnesium sulphate and then concentrated. The desired product is obtained by purification by chromatography on silica gel using an 8:2 heptane/ethyl acetate mixture as eluant.

Step g: tert-Butyl(1R,2S,5R)- and (1S,2R,5S)-2-[(4-biphenyl)sulphanyl]-5-(tosyloxymethyl)-1-cyclopentanecarboxylate Pyridine (42 μl; 0.53 mmol) and para-toluenesulphonyl chloride (69 mg; 0.36 mmol) are added to a solution of 0.176 mmol (70 mg) of the alcohol obtained in the preceding Step in 5 ml of dichloromethane, and the whole is stirred at ambient temperature for one night. The reaction mixture is then concentrated and subsequently taken up in ethyl acetate. The organic phase is washed with an aqueous 10% hydrochloric acid solution, with a saturated aqueous solution of $NaHCO_3$, and then with a saturated solution of sodium chloride until neutral. After drying over magnesium sulphate and concentration, the expected product is isolated following purification by chromatography on silica gel using a 9:1 heptane/ethyl acetate mixture as eluant.

Step h: tert-Butyl(1R,2S,5R)- and (1S,2R,5S)-2-[(4-biphenyl)sulphanyl]-5-[(1,3-dioxo-2,3-dihydro-1H-2-isoindolyl)methyl]-1-cyclopentanecarboxylate Potassium phthalimidate (58 mg; 0.312 mmol) and then crown ether (18-crown-6) (82 mg; 0.312 mmol) are added to a solution of 0.104 mmol (56 mg) of the compound obtained in the preceding Step in 5 ml of anhydrous dimethylformamide. When the whole has become homogeneous it is heated at 50° C. for 2 hours. The reaction mixture is then concentrated. The expected product is isolated by purification by chromatography on a column of silica gel using a 9:1 heptane/ethyl acetate mixture as eluant.

Step i: (1R,2S,5S)- and (1S,2R,5S)-2-[(4-biphenyl)sulphanyl]-5-[(1,3-dioxo-2,3-dihydro-1H-2-isoindolyl)methyl]-1-cyclopentanecarboxylic acid 0.5 ml of trifluoroacetic acid is added to a solution of 0.055 mmol (30 mg) of the compound obtained in the preceding Step in 5 ml of dichloromethane at 0° C. under argon and the whole is stirred, while allowing a progressive return to ambient temperature, for 12 hours. The reaction mixture is then concentrated to yield the expected compound.

Melting point: 146–148° C.

Elemental microanalysis

|  | C | H | N | S |
|---|---|---|---|---|
| % calculated | 70.88 | 5.07 | 3.06 | 7.01 |
| % found | 70.48 | 5.14 | 3.09 | 6.76 |

EXAMPLE 2

(1R,2S,5R)- and (1S,2R,5S)-2-[(4-biphenyl)
methylsulphanyl]-5-[(1,3-dioxo-2,3-dihydro-1H-2-
isoindolyl)methyl]-1-cyclopentanecarboxylic acid The expected product is obtained in accordance with the procedure described in Example 1, with the replacement of 4-bromothiophenol in Step e with the compound described in Preparation F.

Elemental microanalysis

|  | C | H | N | S |
|---|---|---|---|---|
| % calculated | 71.32 | 5.34 | 2.97 | 6.80 |
| % found | 71.11 | 5.36 | 3.09 | 6.85 |

EXAMPLE 3

(1R,2S,5R)- and (1S,2R,5S)-2-{2-[(4-biphenyl)
ethyl]sulphanyl}-5-[(1,3-dioxo-2,3-dihydro-1H-2-
isoindolyl)methyl]-1-cyclopentanecarboxylic acid The expected product is obtained in accordance with the procedure described in Example 1, with the replacement of 4-bromothiophenol in Step e with the compound described in Preparation E.

Elemental microanalysis

|  | C | H | N | S |
|---|---|---|---|---|
| % calculated | 71.73 | 5.60 | 2.88 | 6.60 |
| % found | 71.64 | 5.59 | 3.00 | 6.41 |

The products of Examples 4 to 15 are obtained in accordance with the procedure described in Example 1, with the replacement of potassium phthalidimate in Step h with the salt of the appropriate compound.

EXAMPLE 4

(1S,2R,5S)- and (1R,2S,5R)-2-[(4-amino-1,3-dioxo-
2,3-dihydro-1H-2-isoindolyl)methyl}-5-[(4-
biphenyl)sulphanyl]-1-cyclopentanecarboxylic acid

EXAMPLE 5

(1S,2R,5S)- and (1R,2S,5R)-2-[(5-amino-1,3-dioxo-
2,3-dihydro-1H-2-isoindolyl)methyl]-5-[(4-
biphenyl)sulphanyl]-1-cyclopentanecarboxylic acid

EXAMPLE 6

(1S,2R,5S)- and (1R,2S,5R)-2-[(4-biphenyl)
sulphanyl]-5-[(1,3-dioxo-2,3-dihydro-1H-pyrrolo[3,
4-c]pyridin-2-yl)methyl]-1-cyclopentanecarboxylic
acid

EXAMPLE 7

(1S,2R,5S)- and (1R,2S,5R)-2-[(4-biphenyl)
sulphanyl]-5-[(1-oxo-2,3-dihydro-1H-2-isoindolyl)
methyl]-1-cyclopentanecarboxylic acid

EXAMPLE 8

(1S,2R,5S)- and (1R,2S,5R)-2-[(4-biphenyl)
sulphanyl]-5-[(1,1,3-trioxo-2,3-dihydro-1H-1λ6-
benzo[d]isothiazol-2-yl)methyl]-1-
cyclopentanecarboxylic acid

EXAMPLE 9

(1S,2R,5S)- and (1R,2S,5R)-2-[(4-biphenyl)
sulphanyl]-5-[(1-oxo-1,2-dihydro-2-phthalazinyl)
methyl]-1-cyclopentanecarboxylic acid

EXAMPLE 10

(1S,2R,5S)- and (1R,2S,5R)-2-[(4-biphenyl)
sulphanyl]-5-[(4-oxo-3,4-dihydro-1,2,3-
benzotriazin-3-yl)methyl]-1-cyclopentanecarboxylic
acid

EXAMPLE 11

(1S,2R,5S)- and (1R,2S,5R)-2-[(4-biphenyl)
sulphanyl]-5-[(2,4-dioxo-3,4-dihydro-2H-1,3-
benzoxazin-3-yl)methyl]-1-cyclopentanecarboxylic
acid

EXAMPLE 12

(1S,2R,5S)- and (1R,2S,5R)-2-[(4-biphenyl)
sulphanyl]-5-[(2,4-dioxo-1,2,3,4-tetrahydro-3-
quinazolinyl)methyl]-1-cyclopentanecarboxylic acid

EXAMPLE 13

(1S,2R,5S)- and (1R,2S,5R)-2-[(4-biphenyl)
sulphanyl]-5-[(5,5-dimethyl-2,4-dioxo-1,3-oxazolan-
3-yl)methyl]-1-cyclopentanecarboxylic acid

EXAMPLE 14

(1S,2R,5S)- and (1R,2S,5R)-2-[(4-biphenyl)
sulphanyl]-5-[(4,4-dimethyl-2,5-dioxo-1-
imidazolidinyl)methyl]-1-cyclopentanecarboxylic
acid

EXAMPLE 15

(1S,2R,5S)- and (1R,2S,5R)-2-[(4-biphenyl)
sulphanyl]-5-[(2,4-dioxo-1,3-thiazolan-3-yl)methyl]-
1-cyclopentanecarboxylic acid

EXAMPLE 16

(1S,2R,5S)- and (1R,2S,5R)-2-[(4-biphenyl)
sulphanyl]-5-[(1,3-dioxo-2,3-dihydro-1H-2-
isoindolyl)methyl]-N-hydroxy-1-
cyclopentanecarboxamide Step a: (1S,2R,5S)- and (1R,2S,5R)-N-allyloxy-2-[(4-
biphenyl)sulphanyl]-5-[(1,3-dioxo-2,3-dihydro-1H-2-
isoindolyl)methyl]-1-cyclopentanecarboxamide Diisopropylethylamine (10.8 mmol, 1.4 g), EDC (1.3 mmol, 0.25 g) and HOBT (1.3 mmol, 0.18 g) are added in succession to solution of the compound obtained in Example 1 (1.08 mmol, 0.5 g) in 50 ml of dichloromethane at 0° C., followed by O-allyl-hydroxylamine hydrochloride (2.17 mmol, 0.24 g). The whole is stirred for 24 hours while allowing a progressive return to ambient temperature. The reaction mixture is then hydrolysed with a 1M aqueous hydrochloric acid solution and extracted several times with dichloromethane. The organic phase is washed with a saturated aqueous solution of $NaHCO_3$, and then with a saturated aqueous solution of sodium chloride until neutral. After drying over magnesium sulphate and concentration, the residue is purified by chromatography on silica gel, using a heptane/ethyl acetate mixture as eluant, to yield the expected compound.

Step b: (1S,2R,5S)- and (1R,2S,5R)-2-[(4-biphenyl)sulphanyl]-5-[(1,3-dioxo-2,3-dihydro-1H-2-isoindolyl)methyl]-N-hydroxy-1-cyclopentanecarboxamide The catalyst $(Pd(PPh_3)_2Cl_2$ (0.03 mmol, 21.5 mg), acetic acid (1.91 mmol, 0.11 ml) and tributyltin hydride (1.53 mmol, 0.4 ml) are added in succession to a solution of 0.85 mmol (424 mg) of the compound described in the preceding Step in 25 ml of dichloromethane. Once the addition is complete the reaction mixture, which has become homogeneous, is stirred at ambient temperature for 1 hour. When the starting material has disappeared completely, the reaction mixture is concentrated and the residue is taken up in acetonitrile and washed with cyclohexane. The acetonitrile is then evaporated off and the expected product is obtained by purification by chromatography on silica gel using a 98:2 dichloromethane/ethyl acetate mixture as eluant.

The compounds described in Examples 17 to 19 are obtained in accordance with the procedure described in Example 16, using as starting material the corresponding acids described in the preceding Examples.

EXAMPLE 17

(1S,2R,5S)- and (1R,2S,5R)-2-[(4-biphenyl)sulphanyl]-5-[(1,3-dioxo-2,3-dihydro-1H-2-pyrrolo[3,4-c]pyridin-2-yl)methyl]-1-cyclopentanecarbohydroxamic acid

EXAMPLE 18

(1S,2R,5S)- and (1R,2S,5R)-2-[(4-biphenyl)sulphanyl]-5-[(1,1,3-trioxo-2,3-dihydro-1H-λ6-benzo[d]isothiazol-2-yl)methyl]-1-cyclopentanecarbohydroxamic acid

EXAMPLE 19

(1S,2R,5S)- and (1R,2S,5R)-2-[(4-biphenyl)sulphanyl]-5-[(4,4-dimethyl-2,5-dioxo-1-imidazolidinyl)methyl]-1-cyclopentanecarbohydroxamic acid

EXAMPLE 20

(1S,2R,5S)- and (1R,2S,5R)-2-[(4-biphenyl)methoxycarbonyl]-5-[(1,3-dioxo-2,3-dihydro-1H-2-isoindolyl)methyl]-1-cyclopentanecarboxylic acid Step a: Benzyl(1S,2R,5S)- and (1R,2S,5R)-2-(hydroxymethyl)-5-(tosyloxymethyl)-1-cyclopentanecarboxylate There are added in succession to a solution of 19.5 mmol (5.15 g) of the compound described in Preparation B in 500 ml of dichloromethane at 0° C., 97.8 mmol (7.87 ml) of pyridine, 1.95 mmol (0.238 g) of dimethylaminopyridine and, dropwise, a solution of 19.5 mmol (3.72 g) of para-toluenesulphonyl chloride in 500 ml of dichloromethane, and the whole is stirred for 5 days while maintaining the temperature at 5° C. The reaction mixture is then hydrolysed with an aqueous 10% hydrochloric acid solution and extracted with dichloromethane. The organic phase is washed with a saturated aqueous solution of sodium chloride and dried over magnesium sulphate. The expected product is obtained by purification by chromatography on silica gel using a 5:1 petroleum ether/ethyl acetate mixture as eluant.

Step b: Benzyl(1R,2R,3S)- and (1S,2S,3R)-1-tert-butoxycarbonyl-3-tosyloxymethyl-2-cyclopentanecarboxylate A solution of 36.3 mmol (3.63 g) of chromic anhydride and 72.5 mmol (5.85 ml) of pyridine in a mixture of 110 ml of dichloromethane and 30 ml of anhydrous dimethylformamide is stirred for 30 minutes at ambient temperature. A solution of 9.1 mmol (3.8 g) of the compound described in the preceding Step in a mixture of 110 ml of dichloromethane and 30 ml of anhydrous dimethylformamide is slowly added thereto. Finally, 72.6 mmol (6.86 ml) of acetic anhydride and 363 mmol (34.2 ml) of tert-butyl alcohol are added and the whole is stirred for 5 days. After hydrolysis in 200 ml of an aqueous 10% hydrochloric acid solution, the reaction mixture is stirred for 30 minutes. The mixture is extracted several times with dichloromethane. The organic phase is washed with a saturated aqueous solution of sodium chloride until neutral and dried over magnesium sulphate. After removal of the solvent by evaporation, the expected product is obtained following purification by chromatography on silica gel using a 95:5 heptane/ethyl acetate mixture as eluant.

Step c: Benzyl(1R,2R,3S)- and (1S,2S,3R)-1-tert-butoxycarbonyl-3-[(1,3-dioxo-2,3-dihydro-1H-2-isoindolyl)methyl]-2-cyclopentanecarboxylate The expected product is obtained using the procedure described in Example 1, Step h, employing as starting material the compound described in the above Step.

Step d: (1S,2R,5S)- and (1R,2S,5R)-2-tert-butoxycarbonyl-5-[(1,3-dioxo-2,3-dihydro-1H-2-isoindolyl)methyl]-1-cyclopentanecarboxylic acid 1.4 g of 10% palladium-on-carbon are added to a solution of 3.02 mmol (1.5 g) of the compound described in the preceding Step in 75 ml of ethanol, and then the whole is stirred at ambient temperature under a hydrogen pressure of 0.4 bar for 2 hours. The reaction mixture is then filtered and concentrated to yield the expected compound.

Step e: Allyl(1R,2R,3S)- and (1S,2S,3R)-1-tert-butoxycarbonyl-3-[(1,3-dioxo-2,3-dihydro-1H-2-isoindolyl)methyl]-2-cyclopentanecarboxylate 3 mmol (0.6 g) of EDC are added to a solution of 2.8 mmol (1.04 g) of the compound described in the preceding Step in 100 ml of dichloromethane at 0° C. When the solution has become homogeneous, 3.35 mmol (0.23 ml) of allyl alcohol are added dropwise followed by 0.27 mmol (33 mg) of DMAP. The reaction mixture is then stirred for 2 hours at ambient temperature, hydrolysed cold with an aqueous 10% hydrochloric acid solution and extracted with dichloromethane. The organic phase is washed with a saturated aqueous solution of sodium chloride until neutral and dried over magnesium sulphate. After concentration, the expected product is isolated following purification by chromatography on silica gel using an 8:2 heptane/ethyl acetate mixture as eluant.

Step f: (1R,2R,3S)- and (1S,2S,3R)-2-allyloxycarbonyl-3-[(1,3-dioxo-2,3-dihydro-1H-2-isoindolyl)methyl]-1-cyclopentanecarboxylic acid The expected product is obtained in accordance with the procedure described in Example 1, Step i, using as starting material the compound described in the above Step.

Step g: Allyl(1R,2R,3S)- and (1S,2S,3R)-1-[(4-biphenyl)methoxycarbonyl]-3-[(1,3-dioxo-1,3-dihydro-2-isoindolyl)methyl]-2-cyclopentanecarboxylate The expected product is obtained in accordance with the procedure described in Step e. using as substrate the compound described in the above Step and with the replacement of allyl alcohol with 4-biphenylmethanol.

Step h: (1S,2R,5S)- and (1R,2S,5R)-2-[(4-biphenyl)methoxycarbonyl]-5-[(1,3-dioxo-1,3-dihydro-2-isoindolyl)methyl]-1-cyclopentanecarboxylic acid The expected product is obtained in accordance with the procedure described in Example 16, Step b, using as starting material the compound described in the above Step.

| Elemental microanalysis | | | |
|---|---|---|---|
| | C | H | N |
| % calculated | 72.04 | 5.21 | 2.90 |
| % found | 72.79 | 5.51 | 2.77 |

EXAMPLE 21

(1S,2R,5S)- and (1R,2S,5R)-2-[(4'-cyano-4-biphenyl)methoxy-carbonyl]-5-[(1,3-dioxo-2,3-dihydro-1H-2-isoindolyl)methyl]-1-cyclopentanecarboxylic acid The expected product is obtained in accordance with the procedure described in Example 20, with the replacement of 4-biphenylmethanol with 4'-cyano-4-biphenylmethanol in Step g.

| Elemental microanalysis | | | |
|---|---|---|---|
| | C | H | N |
| % calculated | 70.86 | 4.76 | 5.51 |
| % found | 70.40 | 5.03 | 5.38 |

EXAMPLE 22

(1S,2R,5S)- and (1R,2S,5R)-2-[(4'-cyano-4-biphenyl)oxycarbonyl]-5-[(1,3-dioxo-2,3-dihydro-1H-2-isoindolyl)methyl]-1-cyclopentanecarboxylic acid The expected product is obtained in accordance with the procedure described in Example 20, with the replacement of 4-biphenylmethanol with 4'-cyano-4-hydroxybiphenyl in Step g.

| Elemental microanalysis | | | |
|---|---|---|---|
| | C | H | N |
| % calculated | 70.44 | 4.48 | 5.66 |
| % found | 70.75 | 4.64 | 5.40 |

EXAMPLE 23

2-[(4-Biphenyl)ethoxymethyl]-4-(1,3-dioxo-2,3-dihydro-1H-2-isoindolyl)butyric acid Step a: 3-[(4-Biphenyl)ethoxymethyl]-4-penten-1-ol The compound described in Preparation G (1.5 g; 5.53 mmol) is dissolved in 40 ml of toluene. The catalyst $Pd(PPh_3)_4$ (128 mg; 0.11 mmol) as well as phenyltributyltin (3.05 g; 8.3 mmol) and lithium chloride (704 mg; 16.6 mmol) are then added. The reaction mixture is heated at reflux for 18 hours. After cooling, the salts are filtered off and the filtrate is concentrated. The residue is purified by chromatography on silica gel using an 8:2 petroleum ether/ethyl acetate mixture as eluant. The solid obtained is taken up in 60 ml of acetonitrile and washed 3 times with 40 ml of cyclohexane each time. The expected product is obtained after evaporation of the acetonitrile.

Step b: 2-{3-[(4-Biphenyl)ethoxymethyl]-4-pentenyl}-1,3-dioxo-2,3-1H-2-isoindolinedione A solution of 2.48 mmol (0.65 g) of triphenylphosphine and 2.48 mmol (0.43 g) of DEAD in 10 ml of tetrahydrofuran is stirred at 0° C. for 30 minutes. There is then added dropwise thereto in the course of 10 minutes a mixture of 1.65 mmol (0.24 g) of phthalimide and 1.65 mmol (0.47 g) of the compound described in the preceding Step dissolved in 10 ml of tetrahydrofuran. The mixture is stirred for 1 hour at 0° C. and then for 1 hour at ambient temperature. The solvents are evaporated off before purifying the residue by chromatography on silica gel, using a 9:1 petroleum ether/ethyl acetate mixture as eluant, to yield the expected compound.

Step c: 2-[(4-Biphenyl)ethoxymethyl]-4-(1,3-dioxo-2,3-dihydro-1H-2-isoindolyl)butyric acid 0.64 mmol (256 mg) of the product described in the preceding Step and 2.64 mmol (565 mg) of $NaIO_4$ are added to a mixture of three solvents: carbon tetrachloride (2 ml), acetonitrile (2 ml), water (3 ml). The biphasic mixture is stirred vigorously and then 0.014 mmol (3 mg) of $RuCl_3 \cdot H_2O$ is added. After reaction for 18 hours, the mixture is diluted with 10 ml of dichloromethane and the phases are separated. The aqueous phase is extracted 3 times with 5 ml of dichloromethane each time. The organic phases are combined, dried over magnesium sulphate and concentrated. The residue is taken up in 20 ml of dichloromethane and filtered through a bed of Celite, and then the solvents are evaporated off. The expected compound is obtained by purification by chromatography on silica gel using an 80:20:1 dichloromethane/ethyl acetate/acetic acid mixture as eluant.

EXAMPLE 24

2-[(4-Biphenyl)ethoxymethyl]-4-(1,3-dioxo-2,3-dihydro-1H-2-isoindolyl)-N-hydroxybutyramide The expected product is obtained in accordance with the procedure described in Example 16, using as starting material the compound described in Example 23.

EXAMPLE 25

2-[(4-Biphenyl)ethoxymethyl]-4-(3,4,4-trimethyl-2,5-dioxo-1-imidazolidinyl)butyric acid The expected product is obtained in accordance with the procedure described in Example 23, with the replacement of phthalimide with 1,5,5-trimethyl-imidazolidine-2,4-dione in Step b.

EXAMPLE 26

2-[(4-Biphenyl)ethoxymethyl]-N-hydroxy-4-(3,4,4-trimethyl-2,5-dioxo-1-imidazolidinyl)butyramide The expected product is obtained in accordance with the procedure described in Example 16, using as starting material the compound described in Example 25.

EXAMPLE 27

2-[(4-Biphenyl)oxymethyl]-4-(4-oxo-3,4-dihydro-1,
2,3-benzotriazin-3-yl)butyric acid The expected product is obtained in accordance with the procedure described in Example 23, using as starting material the compound described in Preparation C and with the replacement of phthalimide with 3H-benzo[1,2,3]triazin-4-one in Step b.

| Elemental microanalysis | | | |
|---|---|---|---|
| | C | H | N |
| % calculated | 69.39 | 5.09 | 10.11 |
| % found | 67.94 | 4.98 | 9.60 |

EXAMPLE 28

2-[(4-Biphenyl)oxymethyl]-N-hydroxy-4-(4-oxo-3,
4-dihydro-1,2,3-benzotriazin-3-yl)butyramide The expected product is obtained in accordance with the procedure described in Example 16, using as starting material the compound described in Example 27.

| Elemental microanalysis | | | |
|---|---|---|---|
| | C | H | N |
| % calculated | 66.97 | 5.15 | 13.02 |
| % found | 66.76 | 5.27 | 12.85 |

EXAMPLE 29

2-[(4-Biphenyl)oxymethyl]-4-(1-oxo-1,2-dihydro-2-
phthalazinyl)butyric acid

The expected product is obtained in accordance with the procedure described in Example 23, using as starting material the compound described in Preparation C and with the replacement of phthalimide with 2H-phthalazin-1-one in Step b.

| Elemental microanalysis | | | |
|---|---|---|---|
| | C | H | N |
| % calculated | 72.45 | 5.35 | 6.76 |
| % found | 72.19 | 5.76 | 6.48 |

EXAMPLE 30

2-[(4-Biphenyl)oxymethyl]-N-hydroxy-4-(1-oxo-1,
2-dihydro-2-phthalazinyl)butyramide The expected product is obtained in accordance with the procedure described in Example 16, using as starting material the compound described in Example 29.

| Elemental microanalysis | | | |
|---|---|---|---|
| | C | H | N |
| % calculated | 69.92 | 5.40 | 9.78 |
| % found | 69.07 | 5.42 | 8.95 |

EXAMPLE 31

2-[(4-Biphenyl)oxymethyl]-4-(1,3-dioxo-2,3-
dihydro-1H-pyrrolo[3,4-c]pyridin-2-yl)butyric acid The expected product is obtained in accordance with the procedure described in Example 23, using as starting material the compound described in Preparation C and with the replacement of phthalimide with pyrrolo[3,4-c]pyridine-1,3-dione in Step b.

| Elemental microanalysis | | | |
|---|---|---|---|
| | C | H | N |
| % calculated | 69.22 | 4.84 | 6.73 |
| % found | 68.54 | 5.04 | 6.48 |

EXAMPLE 32

2-[(4-Biphenyl)oxymethyl]-N-hydroxy-4-(1,3-
dioxo-2,3-dihydro-1H-pyrrolo[3,4-c]pyridin-2-yl)
butyramide The expected product is obtained in accordance with the procedure described in Example 16, using as starting material the compound described in Example 31.

EXAMPLE 33

4-(Benzoylamino)-2-[(4-biphenyl)ethoxymethyl]
butyric acid

Step a: 3-[(4-Biphenyl)ethoxymethyl]-4-pentenylamine hydrochloride

A solution of 7.55 mmol (3 g) of the product described in Example 23, Step b, in 10 ml of 1,2-dichloroethane is treated with 8.34 mmol (0.44 ml) of N-methylhydrazine and then heated at reflux for 24 hours. After cooling, the mixture is filtered. The solid is washed with dichloromethane (2×5 ml). The organic phases are combined and concentrated. The residue is redissolved in diethyl ether, and then the hydrochloride is precipitated by the addition of an ethereal hydrogen chloride solution. The expected product is obtained by filtration and drying.

Step b: N-{3-[(4-Biphenyl)ethoxymethyl]-4-pentenyl}benzamide

A mixture of 2.63 mmol (0.8 g) of the product obtained in the preceding Step and 5.58 mmol (0.52 g) of pyridine in 20 ml of dichloromethane is cooled to 0° C. before being treated with 2.90 mmol (0.41 g) of benzoyl chloride. The reaction mixture is then stirred for 1 hour at 0° C. and subsequently for 1 hour at ambient temperature. The mixture is diluted with 10 ml of dichloromethane before being washed in succession with water, an aqueous molar solution of hydrochloric acid, an aqueous molar solution of sodium hydroxide and then a saturated aqueous solution of sodium chloride. After drying over magnesium sulphate and concentration in vacuo, the residue obtained is purified by chromatography on silica gel to yield the expected compound.

Step c: 4-(Benzoylamino)-2-[(4-biphenyl)ethoxymethyl]butyric acid

The expected product is obtained in accordance with the procedure described in Example 23, Step c, using as starting material the compound described in the above Step.

EXAMPLE 34

4-(Benzoylamino)-2-[(4-biphenyl)ethoxymethyl]-N-hydroxybutyric acid

The expected product is obtained in accordance with the procedure described in Example 16, using as starting material the compound described in Example 33.

EXAMPLE 35

2-[(4-Biphenyl)ethoxymethyl]-4-{[(4-methoxyphenyl)sulphonyl]amino}butyric acid

The expected product is obtained using the procedure described in Example 33, with the replacement of benzoyl chloride with 4-methoxybenzenesulphonyl chloride in Step b.

EXAMPLE 36

2-[(4-Biphenyl)ethoxymethyl]-N-hydroxy-4-{[(4-methoxyphenyl]sulphonyl]amino}butyramide The expected product is obtained in accordance with the procedure described in Example 16, using as starting material the compound described in Example 35.

EXAMPLE 37

2-[(4-Biphenyl)oxymethyl]-5-(1,3-dioxo-2,3-dihydro-1H-2-isoindolyl)pentanoic acid
Step a: 4-[(4-Biphenyl)oxymethyl]-5-hexenenitrile The expected product is obtained in accordance with the procedure described in Example 23, Steps a and b, using as starting material in Step a the compound described in Preparation C and with the replacement of phthalimide with acetone cyanohydrin in Step b.
Step b: 4-[(4-Biphenyl)oxymethyl]-5-hexenylamine hydrochloride A solution of 2.24 mmol (0.62 g) of the compound described in the preceding Step in 15 ml of diethyl ether is cooled to 0° C. using an ice-bath. A suspension of 2.24 mmol (84 mg) of lithium aluminium hydride in 5 ml of diethyl ether is slowly added and the reaction mixture is then stirred for 2 hours at 0° C. and subsequently for 1 hour 30 minutes at ambient temperature. The mixture is then hydrolysed with water and extracted with dichloromethane. The organic phases are washed with a saturated aqueous solution of sodium chloride, dried over magnesium sulphate and concentrated. The residue is taken up in diethyl ether, and then the hydrochloride is precipitated by the addition of ethereal hydrogen chloride before being filtered to yield the expected compound.
Step c: 2-{4-[(4-Biphenyl)oxymethyl]-5-hexenyl}-]1,3-isoindolinedione A solution of 1.25 mmol (0.4 g) of the compound described in the preceding Step in 15 ml of tetrahydrofuran in the presence of 3.15 mmol (0.32 g) of triethylamine and 1.38 mmol (0.3 g) of N-(ethoxycarbonyl)phthalimide is heated at reflux for a whole day with vigorous stirring. After cooling, the mixture is filtered and the filtrate is concentrated. The residue is taken up in dichloromethane and washed with a 1M aqueous hydrochloric acid solution, and with a saturated aqueous solution of sodium chloride and subsequently dried over magnesium sulphate and concentrated. The expected product is obtained by purification by chromatography on silica gel using a 97:3 petroleum ether/ethyl acetate mixture as eluant.

Step d: 2-[(4-Biphenyl)oxymethyl]-5-(1,3-dioxo-2,3-dihydro-1H-2-isoindolyl)pentanoic acid The expected product is obtained in accordance with the procedure described in Example 23, Step c, using as starting material the compound described in the above Step.

EXAMPLE 38

2-[(4-Biphenyl)oxymethyl]-5-(1,3-dioxo-2,3-dihydro-1H-2-isoindolyl)-N-hydroxypentanamide The expected product is obtained in accordance with the procedure described in Example 16, using as starting material the compound described in Example 37.

EXAMPLE 39

2-[(4-Biphenyl)sulphanylmethyl]-4-(1,3-dioxo-2,3-dihydro-1H-2-isoindolyl)butyric acid Step a: tert-Butyl 4-hydroxy-2-[(4-bromophenyl)sulphanylmethyl]butyrate A solution of sodium methanolate (55.35 mmol, 3 g) in 20 ml of methanol is added to a solution of para-bromothiophenol (45.1 mmol, 34.3 g) in 30 ml of anhydrous methanol at 0° C. The whole is stirred at ambient temperature for 1 hour. A solution of the compound described in Preparation D (37.59 mmol, 6.5 g) in 70 ml of methanol is then added and the whole is heated at 60° C. for 1 hour. The reaction mixture is then concentrated to dryness and taken up in water, and subsequently washed with ether. The aqueous phase is acidified with a dilute hydrochloric acid solution and extracted with ethyl acetate. The organic phase is washed with a saturated solution of sodium chloride, dried over magnesium sulphate and concentrated to yield the expected compound.

Step b: Methyl 2-[(4-bromophenyl)sulphanylmethyl]-4-(1,3-dioxo-2,3-dihydro-1H-2-isoindolyl)butyrate The expected product is obtained in accordance with the procedure described in Example 23, Step b, using as starting material the compound described in the above Step.

Step c: Methyl 2-[(4-biphenyl)sulphanylmethyl]-4-(1,3-dioxo-2,3-dihydro-1H-2-isoindolyl)butyrate The expected product is obtained in accordance with the procedure described in Example 23, Step a, using as starting material the compound described in the above Step.

Step d: 2-[(4-Biphenyl)sulphanylmethyl]-4-(1,3-dioxo-2,3-dihydro-1H-2-isoindolyl)butyric acid The expected compound is obtained in accordance with the procedure described in Example 1, Step i, using as starting material the compound described in the above Step.

Melting point: 144° C.

| Elemental microanalysis | | | | |
|---|---|---|---|---|
| | C | H | N | S |
| % calculated | 69.59 | 4.91 | 3.25 | 7.43 |
| % found | 69.08 | 4.91 | 3.25 | 7.43 |

EXAMPLE 40

2-[(4-Biphenyl)sulphanylmethyl]-4-(1,3-dioxo-2,3-dihydro -1H-2-isoindolyl)-N-hydroxybutyramide The expected product is obtained in accordance with the procedure described in Example 16, using as starting material the compound described in Example 39.

Mass spectrum (IE): m/z=446.1281 (theoretical mass: 446.1300)

EXAMPLE 41

2-[(4-Biphenyl)sulphanylmethyl]-4-(3,4,4-trimethyl-2,5-dioxo-1-imidazolidinyl)butyric acid Step a: Methyl 2-[(4-bromophenyl)sulphanylmethyl]-4-(3, 4,4-trimethyl-2,5-dioxo-1-imidazolidinyl)butyrate The expected product is obtained in accordance with the procedure described in Example 39, Step a and Step b, with the replacement of phthalimide with 1,5,5-trimethylimidazolidine-2,4-dione in Step b.

Step b: 2-[(4-Biphenyl)sulphanylmethyl]-4-(3,4,4-trimethyl-2,5-dioxo-1-imidazolidinyl)butyric acid A solution of 0.63 mmol (0.28 g) of the compound described in the preceding Step in 2 ml of dioxane is treated with 3 ml of a 0.5M aqueous sodium hydroxide solution. After stirring for 20 minutes, the mixture is acidified with an aqueous molar solution of hydrochloric acid and then extracted with diethyl ether. The organic phases are dried over magnesium sulphate and concentrated. The residue is purified by chromatography on silica gel, using a 90:10:0.1 dichloromethane/methanol/acetic acid mixture as eluant, to yield the expected compound.

Melting point: 163° C.

| Elemental microanalysis | | | | |
|---|---|---|---|---|
| | C | H | N | S |
| % calculated | 64.77 | 6.14 | 6.57 | 7.52 |
| % found | 64.02 | 6.14 | 6.42 | 7.85 |

EXAMPLE 42

2-[(4-Biphenyl)sulphanylmethyl]-N-hydroxy-4-(3,4,4-trimethyl-2,5-dioxo-1-imidazolidinyl)butyramide The expected product is obtained in accordance with the procedure described in Example 16, using as starting material the compound described in Example 41.

EXAMPLE 43

2-[(4-Biphenyl)sulphonylmethyl]-4-(1,3-dioxo-2,3-dihydro-1H-2-isoindolyl)butyric acid Step a: Methyl 2-[(4-biphenyl)sulphonylmethyl]-4-(1,3-dioxo-2,3-dihydro-1H-2-isoindolyl)butyrate A solution of 2.2 mmol (1 g) of the compound described in Example 39, Step b, in 25 ml of dichloromethane is treated with 4.96 mmol (1.76 g) of tetrabutylammonium oxone. The reaction mixture is stirred for 3 days at ambient temperature. After removal of the solvents by evaporation, the residue is purified by chromatography on silica gel, using an 8:2 petroleum ether/ethyl acetate mixture as eluant, to yield the expected compound.

Step b: 2-[(4-Biphenyl)sulphonylmethyl]-4-(1,3-dioxo-2,3-dihydro-1H-2-isoindolyl)butyric acid The expected product is obtained in accordance with the procedure described in Example 39, Step d, using as starting material the compound described in the above Step.

Melting point: 180° C.

| Elemental microanalysis | | | | |
|---|---|---|---|---|
| | C | H | N | S |
| % calculated | 64.78 | 4.57 | 3.02 | 6.92 |
| % found | 64.92 | 4.76 | 3.06 | 7.05 |

EXAMPLE 44

2-[(4-Biphenyl)sulphonylmethyl]-4-(1,3-dioxo-2,3-dihydro-1H-2-isoindolyl)-N-hydroxybutyramide The expected product is obtained in accordance with the procedure described in Example 16, using as starting material the compound described in Example 43.

EXAMPLE 45

2-{2-[(4-Biphenyl)ethyl]sulphanylmethyl}-4-(1,3-dioxo-2,3-dihydro-1H-2-isoindolyl)butyric acid The expected product is obtained in accordance with the procedure described in Example 39, using as starting material the compound described in Preparation E.

EXAMPLE 46

2-{2-[(4-Biphenyl)ethyl]sulphanylmethyl}-4-(1,3-dioxo-2,3-dihydro-1H-2-isoindolyl)-N-hydroxybutyramide The expected product is obtained in accordance with the procedure described in Example 16, using as starting material the compound described in Example 45.

EXAMPLE 47

2-[(4-Biphenyl)methylsulphanylmethyl]-4-(1,3-dioxo-2,3-dihydro-1H-2-isoindolyl)butyric acid The expected product is obtained in accordance with the procedure described in Example 39, using as starting material the compound described in Preparation F.

Melting point: 119° C.

| Elemental microanalysis | | | | |
|---|---|---|---|---|
| | C | H | N | S |
| % calculated | 70.09 | 5.20 | 3.14 | 7.20 |
| % found | 70.21 | 5.35 | 3.19 | 7.13 |

EXAMPLE 48

2-[(4-Biphenyl)methylsulphanylmethyl]-4-(1,3-dioxo-2,3-dihydro-1H-2-isoindolyl)-N-hydroxybutyramide The expected product is obtained in accordance with the procedure described in Example 16, using as starting material the compound described in Example 47.

| Elemental microanalysis | | | | |
|---|---|---|---|---|
| | C | H | N | S |
| % calculated | 67.81 | 5.25 | 6.08 | 6.96 |
| % found | 66.47 | 5.15 | 5.96 | 6.85 |

EXAMPLE 49

(1R,2S,5R)- and (1S,2R,5S)-2-[(4'-chloro-4-biphenyl)sulphanyl]-5-[(4-oxo-3,4-dihydro-1,2,3-benzotriazin-3-yl)methyl]-1-cyclopentanecarboxylic acid Step a: tert-Butyl(1R,2S,5R)- and (1S,2R,5S)-2-[(4-bromophenyl)sulphanyl]-5-[(4-oxo-3,4-dihydro-1,2,3-benzotriazin-3-yl)methyl]-1-cyclopentanecarboxylate The expected product is obtained in accordance with the procedure described in Example 23, Step b, with the replacement of phthalimide with 3H-benzo[1,2,3]triazin-4-one and using as starting material the compound described in Example 1, Step e.

Step b: tert-Butyl(1R,2S,5R)- and (1S,2R,5S)-2-[(4'-chloro-4-biphenyl)sulphanyl]-5-[4-oxo-3,4-dihydro-1,2,3-benzotriazin-3-yl)methyl]-1-cyclopentanecarboxylate The expected product is obtained in accordance with the procedure described in Example 23, Step a, using as starting material the compound described in the above Step and with the replacement of phenyltributyltin with 4-chlorophenyltributyltin.

Step c: (1R,2S,5R)- and (1S,2R,5S)-2-[(4'-chloro-4-biphenyl)sulphanyl]-5-[(4-oxo-3,4-dihydro -1,2,3-benzotriazin-3-yl)methyl]-1-cyclopentanecarboxylic acid The expected product is obtained in accordance with the procedure described in Example 1, Step i, using as starting material the compound described in the above Step.

| Elemental microanalysis | | | | | |
|---|---|---|---|---|---|
| | C | H | N | Cl | S |
| % calculated | 63.47 | 4.51 | 8.54 | 7.21 | 6.52 |
| % found | 63.80 | 4.53 | 8.72 | 7.29 | 6.65 |

EXAMPLE 50

(1R,2S,5R)- and (1S,2R,5S)-2-[(4'-chloro-4-biphenyl)sulphanyl]-N-hydroxy-5-[(4-oxo-3,4-dihydro-1,2,3-benzotriazin-3-yl)methyl]-1-cyclopentanecarboxamide The expected product is obtained in accordance with the procedure described in Example 16, using as starting material the compound described in Example 49.

| Elemental microanalysis | | | | |
|---|---|---|---|---|
| | C | H | N | S |
| % calculated | 61.59 | 4.57 | 11.05 | 6.32 |
| % found | 60.20 | 4.49 | 10.78 | 6.31 |

EXAMPLE 51

(1R,2S,5R)- and (1S,2R,5S)-2-[(4'-chloro-4-biphenyl)sulphonyl]-5-[(4-oxo-3,4-dihydro-1,2,3-benzotriazin-3-yl)methyl]-1-cyclopentanecarboxylic acid The expected product is obtained in accordance with the procedure described in Example 43, using as starting material the compound described in Example 49.

| Elemental microanalysis | | | | | |
|---|---|---|---|---|---|
| | C | H | N | Cl | S |
| % calculated | 59.60 | 4.23 | 8.02 | 6.77 | 6.12 |
| % found | 59.59 | 4.29 | 7.94 | 6.65 | 6.18 |

EXAMPLE 52

(1R,2R,5R)- and (1S,2S,5S)-2-[(4'-chloro-4-biphenyl)sulphanyl]-[(4-oxo-3,4-dihydro-1,2,3-benzotriazin-3-yl)methyl]-1-cyclopentanecarboxylic acid The expected product is obtained in accordance with the procedure described in Example 49, using as starting material tert-butyl(1R,2R,5R)- and (1S,2R,5S)-2-(4-bromophenylsulphanyl)-5-(hydroxymethyl)-1-cyclopentanecarboxylate, the diastereoisomer isolated during the course of the preparation of the compound described in Example 1, Step e.

| Elemental microanalysis | | | | | |
|---|---|---|---|---|---|
| | C | H | N | Cl | S |
| % calculated | 63.47 | 4.51 | 8.54 | 7.21 | 6.52 |
| % found | 63.44 | 4.76 | 8.28 | 7.21 | 6.56 |

EXAMPLE 53

(1R,2S,5R)- and (1S,2R,5S)-2-[2-(4'-chloro-4-biphenyl)ethylsulphanyl]-5-1(4-oxo-3,4-dihydro-1,2,3-benzotriazin-3-yl)methyl]-1-cyclopentanecarboxylic acid The expected product is obtained in accordance with the procedure described in Example 49, using as starting material in Step a tert-butyl 2-[2-(4-bromophenyl)sulphanyl]-5-(hydroxymethyl)-1-cyclopentanecarboxylate (obtained in accordance with the procedure described in Example 1, Step e, and with the replacement of 4-bromothiophenol with the compound described in Preparation E).

| Elemental microanalysis | | | | | |
|---|---|---|---|---|---|
| | C | H | N | Cl | S |
| % calculated | 64.67 | 5.04 | 8.08 | 6.82 | 6.17 |
| % found | 64.43 | 5.04 | 7.99 | 6.87 | 6.05 |

EXAMPLE 54

(1R,2S,5R)- and (1S,2R,5S)-2-[2-(4'-chloro-4-biphenyl)ethylsulphanyl]-N-hydroxy-5-[(4-oxo-3,4-dihydro-1,2,3-benzotriazin-3-yl)methyl]-1-cyclopentanecarboxamide The expected product is obtained in accordance with the procedure described in Example 16, using as starting material the compound described in Example 53.

| Elemental microanalysis | | | | | |
|---|---|---|---|---|---|
| | C | H | N | Cl | S |
| % calculated | 62.85 | 5.09 | 10.47 | 6.63 | 5.99 |
| % found | 62.41 | 5.09 | 10.28 | 7.32 | 5.78 |

EXAMPLE 55

(1R,2S,5R)- and (1S,2R,5S)-2-[2-(4'-chloro-4-biphenyl)ethylsulphonyl]-5-[(4-oxo-3,4-dihydro-1,2,3-benzotriazin-3-yl)methyl]-1-cyclopentanecarboxylic acid The expected product is obtained in accordance with the procedure described in Example 43, using as starting material the compound described in Example 53.

| Mass spectrum: | |
|---|---|
| DCI (NH$_3$): | m/z = 552 (MH$^+$) |
| | m/z = 569 (MNH$_4^+$) |

EXAMPLE 56

(1R,2S,5R)- and (1S,2R,5S)-2-[2-(4'-fluoro-4-biphenyl)ethylsulphanyl]-5-[(4-oxo-3,4-dihydro-1,2,3-benzotriazin-3-yl)methyl]-1-cyclopentanecarboxylic acid The expected product is obtained in accordance with the procedure described in Example 49, using as starting material in Step a tert-butyl 2-[2-(4-bromophenyl)sulphanyl]-5-(hydroxymethyl)-1-cyclopentanecarboxylate (obtained in accordance with the procedure described in Example 1, Step e, with the replacement of 4-bromothiophenol with the compound described in Preparation E), and with the replacement of 4-chlorophenyltributyltin with 4-fluorophenyltributyltin in Step b.

Mass spectrum: DCI (NH$_3$): m/z=521 (MH$^+$)

EXAMPLE 57

(1R,2S,5R)- and (1S,2R,5S)-2-[2-(4-bromophenyl)ethylsulphanyl]-5-[(1,3-dioxo-2,3-dihydro-1H-2-isoindolyl)methyl]-1-cyclopentanecarboxylic acid Step a: tert-Butyl(1R,2S,5R)- and (1S,2R,5S)-2-[2-(4-bromophenyl)ethylsulphanyl]-5-(hydroxymethyl)-1-cyclopentanecarboxylate The expected product is obtained in accordance with the procedure described in Example 1, Step e, with the replacement of 4-bromothiophenol with the compound described in Preparation E.

Step b: tert-Butyl(1R,2S,5R)- and (1S,2R,5S)-2-[2-(4-bromophenyl)ethylsulphanyl]-5-[(1,3-dioxo-2,3-dihydro-1H-2-isoindolyl)methyl]-1-cyclopentanecarboxylate The expected product is obtained in accordance with the procedure described in Example 23, Step b, using as starting material the compound described in the above Step.

Step c: (1R,2S,5R)- and (1S,2R,5S)-2-[2-(4-bromophenyl)ethylsulphanyl]-5-[(1,3-dioxo-2,3-dihydro-1H-2-isoindolyl)methyl]-1-cyclopentanecarboxylic acid The expected product is obtained in accordance with the procedure described in Example 1, Step i, using as starting material the compound described in the above Step.

| Elemental microanalysis | | | | | |
|---|---|---|---|---|---|
| | C | H | N | Br | S |
| % calculated | 56.56 | 4.54 | 2.87 | 16.36 | 6.57 |
| % found | 57.26 | 4.75 | 2.87 | 16.43 | 6.54 |

EXAMPLE 58

(1R,2S,5R)- and (1S,2R,5S)-2-[2-(4'-chloro-4-biphenyl)ethylsulphanyl]-5-[(1,3-dioxo-2,3-dihydro-1H-2-isoindolyl)methyl]-1-cyclopentanecarboxylic acid Step a: tert-Butyl(1R,2S,5R)- and (1S,2R,5S)-2-[2-(4'-chloro-4-biphenyl)ethylsulphanyl]-5-[(1,3-dioxo-2,3-dihydro-1H-2-isoindolyl)methyl]-1-cyclopentanecarboxylate The expected product is obtained in accordance with the procedure described in Example 23, Step a, using as starting material the compound described in Example 57, Step b, and with the replacement of phenyltributyltin with 4-chlorophenyltributyltin.

Step b: (1R,2S,5R)- and (1S,2R,5S)-2-[2-(4'-chloro-4-biphenyl)ethylsulphanyl]-5-[(1,3-dioxo-2,3-dihydro-1H-2-isoindolyl)methyl]-1-cyclopentanecarboxylic acid The expected product is obtained in accordance with the procedure described in Example 1, Step i, using as starting material the compound described in the above Step.

| Elemental microanalysis | | | | | |
|---|---|---|---|---|---|
| | C | H | N | Br | S |
| % calculated | 66.98 | 5.04 | 2.69 | 6.82 | 6.17 |
| % found | 66.69 | 5.19 | 2.69 | 6.76 | 6.07 |

EXAMPLE 59

(1R,2S,5R)- and (1S,2R,5S)-2-[2-(4'-fluoro-4-biphenyl)ethylsulphanyl]-5-[(1,3-dioxo-2,3-dihydro-1H-2-isoindolyl)methyl]-1-cyclopentanecarboxylic acid The expected product is obtained in accordance with the procedure described in Example 58, with the replacement of 4-chlorophenyltributyltin with 4-fluorophenyltributyltin.

| | Elemental microanalysis | | | |
|---|---|---|---|---|
| | C | H | N | S |
| % calculated | 69.17 | 5.20 | 2.78 | 6.37 |
| % found | 69.87 | 5.30 | 3.21 | 5.93 |

EXAMPLE 60

(1R,2S,5R)- and (1S,2R,5S)-2-[2-(4-biphenyl)ethylsulphanyl]-5-[(1,3-dioxo-2,3-dihydro-1H-2-isoindolyl)methyl]-N-hydroxy-1-cyclopentanecarboxamide The expected product is obtained in accordance with the procedure described in Example 16, using as starting material the compound described in Example 3.

| | Elemental microanalysis | | | |
|---|---|---|---|---|
| | C | H | N | S |
| % calculated | 69.58 | 5.64 | 5.60 | 6.40 |
| % found | 69.62 | 6.04 | 5.21 | 5.97 |

EXAMPLE 61

(1R,2S,5R)- and (1S,2R,5S)-5-[(4-oxo-3,4-dihydro-1,2,3-benzotriazin-3-yl)methyl]-2-[4-(3-pyridyl)phenylsulphanyl]-1-cyclopentanecarboxylic acid The expected product is obtained in accordance with the procedure described in Example 49, with the replacement of 4-chlorophenyltributyltin with 3-pyridyltributyltin in Step c.

EXAMPLE 62

(1R,2S,5R)- and (1S,2R,5S)-5-[(4-oxo-3,4-dihydro-1,2,3-benzotriazin-3-yl)methyl]-2-[4-(3-thienyl)phenylsulphanyl]-1-cyclopentanecarboxylic acid The expected product is obtained in accordance with the procedure described in Example 49, with the replacement of 4-chlorophenyltributyltin with 3-thienyltributyltin in Step c.

EXAMPLE 63

(1S,2R,5S)- and (1R,2S,5R)-2-[(4-biphenyl)methoxycarbonyl]-5-[(1,3-dioxo-2,3-dihydro-1H-2-isoindolyl)methyl]-N-hydroxy-1-cyclopentanecarboxamide The expected product is obtained in accordance with the procedure described in Example 16, using as starting material the compound described in Example 20.

| | Elemental microanalysis | | |
|---|---|---|---|
| | C | H | N |
| % calculated | 69.87 | 5.26 | 5.62 |
| % found | 69.18 | 5.36 | 5.58 |

In accordance with the procedure described in Example 20 and using the salt of the appropriate compound in Step c, the compounds of Examples 64 to 66 are obtained.

EXAMPLE 64

(1S,2R,5S)- and (1R,2S,5R)-2-[(4-biphenyl)methoxycarbonyl]-5-[(1,3-dioxo-2,3-dihydro-1H-2-pyrrolo[3,4-c]pyridin-2-yl)methyl]-1-cyclopentanecarboxylic acid

EXAMPLE 65

(1S,2R,5S)- and (1R,2S,5R)-2-[(4-biphenyl)methoxycarbonyl]-5-[(4-oxo-3,4-dihydro-1,2,3-benzotriazin-3-yl)methyl]-1-cyclopentanecarboxylic acid

EXAMPLE 66

(1S,2R,5S)- and (1R,2S,5R)-2-[(4-biphenyl)methoxycarbonyl]-5-[(1,1,3-trioxo-2,3-dihydro-1H-λ6-benzo[d]isothiazol-2-yl)methyl]-1-cyclopentanecarboxylic acid Using the procedure described in Example 20 and with the replacement of 4-biphenylmethanol with the appropriate biphenyl compound in Step g, the compounds of Examples 67 to 69 are obtained.

EXAMPLE 67

(1S,2R,5S)- and (1R,2S,5R)-2-[(4'-chloro-4-biphenyl)methoxycarbonyl]-5-[(4-oxo-3,4-dihydro-1,2,3-benzotriazin-3-yl)methyl]-1-cyclopentanecarboxylic acid

EXAMPLE 68

(1S,2R,5S)- and (1R,2S,5R)-2-[(4'-fluoro-4-biphenyl)methoxycarbonyl]-5-[(4-oxo-3,4-dihydro-1,2,3-benzotriazin-3-yl)methyl]-1-cyclopentanecarboxylic acid

EXAMPLE 69

(1S,2R,5S)- and (1R,2S,5R)-2-[(4'-chloro-4-biphenyl)oxycarbonyl]-5-[(4-oxo-3,4-dihydro-1,2,3-benzotriazin-3-yl)methyl]-1-cyclopentanecarboxylic acid

EXAMPLE 70

2-[(4-Biphenyl)oxymethyl]-4-(1,1,3-trioxo-2,3-dihydro-1H-1λ6-benzo[d]isothiazol-2-yl)butyric acid The expected product is obtained in accordance with the procedure described in Example 23, using as starting material the compound described in Preparation C and with the replacement of phthalimide with saccharin in Step b.

EXAMPLE 71

2-[(4-Biphenyl)oxymethyl]-N-hydroxy-4-(1,1,3-trioxo-2,3-dihydro-1H-1λ6-benzo[d]isothiazol-2-yl)butyramide The expected product is obtained in accordance with the procedure described in Example 16, using as starting material the compound described in Example 70.

| Elemental microanalysis | | | | |
|---|---|---|---|---|
| | C | H | N | S |
| % calculated | 61.79 | 4.75 | 6.00 | 6.87 |
| % found | 61.32 | 4.65 | 6.04 | 6.85 |

EXAMPLE 72

2-[(4-Biphenyl)oxymethyl]-4-(2,4-dioxo-1,2,3,4-tetrahydro-3-quinazolinyl)butyric acid The expected product is obtained in accordance with the procedure described in Example 23, using as starting material the compound described in Preparation C and with the replacement of phthalimide with isatoic anhydride in Step b.

EXAMPLE 73

2-[(4-Biphenyl)oxymethyl]-4-(2,4-dioxo-1,2,3,4-tetrahydro-3-quinazolinyl)-N-hydroxybutyramide The expected product is obtained in accordance with the procedure described in Example 16, using as starting material the compound described in Example 72.

| Elemental microanalysis | | | |
|---|---|---|---|
| | C | H | N |
| % calculated | 67.41 | 5.20 | 9.43 |
| % found | 65.38 | 4.89 | 9.25 |

EXAMPLE 74

2-[(4-Bromophenyl)oxymethyl]-4-(4-oxo-3,4-dihydro-1,2,3-benzotriazin-3-yl)butyric acid The expected product is obtained in accordance with the procedure described in Example 23, Steps b and c, using as starting material the compound described in Preparation C and with the replacement of phthalimide with 3H-benzo[1,2,3]triazin-4-one in Step b.

| Elemental microanalysis | | | | |
|---|---|---|---|---|
| | C | H | N | Br |
| % calculated | 51.69 | 3.86 | 10.05 | 19.10 |
| % found | 51.67 | 3.89 | 9.90 | 18.47 |

EXAMPLE 75

2-[(4-Bromophenyl)oxymethyl]-N-hydroxy-4-(4-oxo-3,4-dihydro-1,2,3-benzotriazin-3-yl)butyramide The expected product is obtained in accordance with the procedure described in Example 16, using as starting material the compound described in Example 74.

| Elemental microanalysis | | | | |
|---|---|---|---|---|
| | C | H | N | Br |
| % calculated | 49.90 | 3.95 | 12.93 | 18.44 |
| % found | 50.19 | 4.13 | 12.43 | 18.19 |

EXAMPLE 76

2-[(4'-Chloro-4-biphenyl)oxymethyl]-4-(4-oxo-3,4-dihydro-1,2,3-benzotriazin-3-yl)butyric acid The expected product is obtained in accordance with the procedure described in Example 23, using as starting material the compound described in Preparation C and with the replacement of phenyltributyltin with 4-chlorophenyltributyltin in Step a and of phthalimide with 3H-benzo[1,2,3]triazin-4-one in Step b.

EXAMPLE 77

2-[(4'-Chloro-4-biphenyl)oxymethyl]-N-hydroxy-4-(4-oxo-3,4-dihydro-1,2,3-benzotriazin-3-yl)butyramide The expected product is obtained in accordance with the procedure described in Example 16, using as starting material the compound described in Example 76.

| Elemental microanalysis | | | | |
|---|---|---|---|---|
| | C | H | N | Cl |
| % calculated | 62.00 | 4.55 | 12.05 | 7.63 |
| % found | 61.81 | 4.55 | 11.91 | 7.68 |

EXAMPLE 78

2-[(4'-Cyano-4-biphenyl)oxymethyl]-4-(4-oxo-3,4-dihydro-1,2,3-benzotriazin-3-yl)butyric acid Step a: 3-{3-[(4'-Bromo-4-biphenyl)oxymethyl]-4-pentenyl}-4-oxo-3,4-dihydro-1,2,3-benzotriazine The expected product is obtained in accordance with the procedure described in Example 23, Steps a and b, using as starting material the compound described in Preparation C and with the replacement of phenyltributyltin with 4-bromophenyltributyltin in Step a and of phthalimide with 3H-benzo[1,2,3]triazin-4-one in Step b.

Step b: 3-{3-[(4'-Cyano-4-biphenyl)oxymethyl]-4-pentenyl}-4-oxo-3,4-dihydro-1,2,3-benzotriazine The expected product is obtained in accordance with the procedure described in Example 23, Step a, with the replacement of phenyltributyltin with zinc dicyanide, without the use of lithium chloride, and using as starting material the compound described in the above Step.

Step c: 2-[(4'-Cyano-4-biphenyl)oxymethyl]-4-(4-oxo-3,4-dihydro-1,2,3-benzotriazin-3-yl)butyric acid The expected product is obtained in accordance with the procedure described in Example 23, Step c, using as starting material the compound described in the above Step.

| Elemental microanalysis | | | |
|---|---|---|---|
| | C | H | N |
| % calculated | 68.17 | 4.58 | 12.72 |
| % found | 67.44 | 4.41 | 12.60 |

EXAMPLE 79

2-[(4'-Cyano-4-biphenyl)oxymethyl]-N-hydroxy-4-(4-oxo-3,4-dihydro-1,2,3-benzotriazin-3-yl)butyramide The expected product is obtained in accordance with the procedure described in Example 16, using as starting material the compound described in Example 78.

| Elemental microanalysis | | | |
|---|---|---|---|
| | C | H | N |
| % calculated | 65.93 | 4.65 | 15.38 |
| % found | 65.24 | 4.84 | 14.58 |

EXAMPLE 80

2-[2-(4'-Chloro-4-biphenyl)ethoxymethyl]-4-(4-oxo-3,4-dihydro-1,2,3-benzotriazin-3-yl)butyric acid The expected product is obtained in accordance with the procedure described in Example 23, with the replacement of phenyltributyltin with 4-chlorophenyltributyltin.

| Elemental microanalysis | | | |
|---|---|---|---|
| | C | H | N | Cl |
| % calculated | 65.33 | 5.06 | 8.79 | 7.42 |
| % found | 65.44 | 5.07 | 8.82 | 7.61 |

EXAMPLE 81

2-[2-(4'-Chloro-4-biphenyl)ethoxymethyl]-N-hydroxy-4-(4-oxo-3,4-dihydro-1,2,3-benzotriazin-3-yl)butyric acid The expected product is obtained in accordance with the procedure described in Example 16, using as starting material the compound described in Example 80.

| Elemental microanalysis | | | |
|---|---|---|---|
| | C | H | N | Cl |
| % calculated | 63.35 | 5.11 | 11.37 | 7.19 |
| % found | 62.95 | 5.07 | 11.27 | 7.54 |

EXAMPLE 82

2-[(4'-Chloro-4-biphenyl)sulphanylmethyl]-4-(1,3-dioxo-2,3-dihydro-1H-2-isoindolyl)butyric acid The expected product is obtained in accordance with the procedure described in Example 39, with the replacement of phenyltributyltin with 4-chlorophenyltributyltin in Step c.

| Elemental microanalysis | | | |
|---|---|---|---|
| | C | H | N | S |
| % calculated | 64.44 | 4.33 | 3.01 | 6.88 |
| % found | 64.12 | 4.40 | 3.09 | 6.91 |

EXAMPLE 83

2-[(4-Bromophenyl)sulphanylmethyl]-4-(4-oxo-3,4-dihydro-1,2,3-benzotriazin-3-yl)butyric acid The expected product is obtained in accordance with the procedure described in Example 39, Steps a, b and d, using 3H-benzo[1,2,3]triazin-4-one instead of phthalimide in Step b.

| Elemental microanalysis | | | | |
|---|---|---|---|---|
| | C | H | N | Br | S |
| % calculated | 49.78 | 3.71 | 9.68 | 18.40 | 7.38 |
| % found | 49.96 | 3.85 | 9.48 | 18.61 | 7.08 |

EXAMPLE 84

2-[(4'-Chloro-4-biphenyl)sulphanylmethyl]-4-(4-oxo-3,4-dihydro-1,2,3-benzotriazin-3-yl)butyric acid The expected product is obtained in accordance with the procedure described in Example 39, using 3H-benzo[1,2,3]triazin-4-one instead of phthalimide in Step b and 4-chlorophenyltributyltin instead of phenyltributyltin in Step c.

EXAMPLE 85

2-[(4'-Chloro-4-biphenyl)sulphanylmethyl]-N-hydroxy-4-(4-oxo-3,4-dihydro-1,2,3-benzotriazin-3-yl)butyramide The expected product is obtained in accordance with the procedure described in Example 16, using as starting material the compound described in Example 84.

| Elemental microanalysis | | | | |
|---|---|---|---|---|
| | C | H | N | Cl | S |
| % calculated | 59.93 | 4.40 | 11.65 | 7.37 | 6.67 |
| % found | 59.28 | 4.47 | 11.17 | 7.38 | 6.45 |

EXAMPLE 86

4-(4-Oxo-3,4-dihydro-1,2,3-benzotriazin-3-yl)-2-[4-(3-pyridyl)phenylsulphanylmethyl)butyric acid trifluoroacetate The expected product is obtained in accordance with the procedure described in Example 39, using 3H-benzo[1,2,3]triazin-4-one instead of phthalimide in Step b and 3-pyridyltributyltin instead of phenyltributyltin in Step c.

| Elemental microanalysis | | | | |
|---|---|---|---|---|
| | C | H | N | S |
| % calculated | 54.94 | 3.87 | 10.09 | 5.62 |
| % found | 54.86 | 3.95 | 10.09 | 5.74 |

EXAMPLE 87

4-(4-Oxo-3,4-dihydro-1,2,3-benzotriazin-3-yl)-2-[4-(3-thienyl)phenylsulphanylmethyl)butyric acid The expected product is obtained in accordance with the procedure described in Example 39, using 3H-benzo[1,2,3]triazin-4-one instead of phthalimide in Step b and 3-thienyltributyltin instead of phenyltributyltin in Step c.

| Elemental microanalysis | | | | |
|---|---|---|---|---|
| | C | H | N | S |
| % calculated | 60.39 | 4.38 | 9.60 | 14.66 |
| % found | 59.93 | 4.54 | 9.65 | 15.23 |

EXAMPLE 88

2-[(4'-Methoxy-4-biphenyl)sulphanylmethyl)-4-(4-oxo-3,4-dihydro-1,2,3-benzotriazin-3-yl)butyric acid Step a: tert-Butyl 4-(4-oxo-3,4-dihydro-1,2,3-benzotriazin-3-yl)-2-{[(4-tributylstannyl)phenyl]sulphanylmethyl)butyrate The expected product is obtained using the procedure described in Example 23, Step a, with the replacement of phenyltributyltin with bis(tributyltin) and using as starting material the tert-butyl ester of the acid described in Example 83.

Step b: tert-Butyl 2-[(4'-methoxy-4-biphenyl)sulphanylmethyl]-4-(4-oxo-3,4-dihydro-1,2,3-benzotriazin-3-yl)butyrate The expected product is obtained using the procedure described in Example 23, Step a, with the replacement of phenyltributyltin with para-iodoanisole and using as starting material the compound described in the above Step.

Step c: 2-[(4'-Methoxy-4-biphenyl)sulphanylmethyl)-4-(4-oxo-3,4-dihydro-1,2,3-benzotriazin-3-yl)butyric acid The expected product is obtained using the procedure described in Example 1, Step i, using as starting material the compound described in the above Step.

| Elemental microanalysis | | | | |
|---|---|---|---|---|
| | C | H | N | S |
| % calculated | 65.06 | 5.02 | 9.10 | 6.95 |
| % found | 64.96 | 5.20 | 8.94 | 7.08 |

EXAMPLE 89

4-(4-Oxo-3,4-dihydro-1,2,3-benzotriazin-3-yl)-2-[4-(5-pyrimidyl)phenylsulphanylmethyl]butyric acid The expected product is obtained using the procedure described in Example 88, with the replacement of para-iodoanisole with 5-bromopyrimidine in Step b.

EXAMPLE 90

N-Hydroxy-4-(4-oxo-3,4-dihydro-1,2,3-benzotriazin-3-yl)-2-[4-(5-pyrimidyl)phenylsulphanylmethyl]butyric acid The expected product is obtained in accordance with the procedure described in Example 16, using as starting material the compound described in Example 89.

| Elemental microanalysis | | | | |
|---|---|---|---|---|
| | C | H | N | S |
| % calculated | 58.92 | 4.49 | 18.74 | 7.15 |
| % found | 58.21 | 4.55 | 17.45 | 7.07 |

EXAMPLE 91

2-{[2-(4'-Fluoro-4-biphenyl)ethyl]sulphanylmethyl}-4-(4-oxo-3,4-dihydro-1,2,3-benzotriazin-3-yl)butyric acid The expected product is obtained in accordance with the procedure described in Example 39, with the replacement of para-bromophenol in Step a with the product described in Preparation E, and using 3H-benzo[1,2,3]triazin-4-one instead of phthalimide in Step b and 4-fluorophenyltributyltin instead of phenyltributyltin in Step c.

| Elemental microanalysis | | | | |
|---|---|---|---|---|
| | C | H | N | S |
| % calculated | 65.39 | 5.07 | 8.80 | 6.71 |
| % found | 65.52 | 5.10 | 8.79 | 6.72 |

EXAMPLE 92

2-{[2-(4'-Chloro-4-biphenyl)ethyl]sulphanylmethyl}-4-(4-oxo-3,4-dihydro-1,2,3-benzotriazin-3-yl)butyric acid The expected product is obtained in accordance with the procedure described in Example 39, with the replacement of para-bromophenol in Step a with the product described in Preparation E, and using 3H-benzo[1,2,3]triazin-4-one instead of phthalimide in Step b and 4-chlorophenyltributyltin instead of phenyltributyltin in Step c.

EXAMPLE 93

2-{[2-(4'-Chloro-4-biphenyl)ethyl]sulphanylmethyl}-N-hydroxy-4-(4-oxo-3,4-dihydro-1,2,3-benzotriazin-3-yl)butyramide The expected product is obtained in accordance with the procedure described in Example 16, using as starting material the compound described in Example 92.

| Elemental microanalysis | | | | | |
|---|---|---|---|---|---|
| | C | H | N | Cl | S |
| % calculated | 61.35 | 4.95 | 11.01 | 6.96 | 6.30 |
| % found | 58.92 | 4.86 | 10.27 | 6.25 | 5.99 |

EXAMPLE 94

2-[(4'-Chloro-4-biphenyl)sulphanylmethyl[-4-[(1,3-dioxo-2,3-dihydro-1H-2-isoindolyl)oxy]butyric acid
Step a: tert-Butyl 2-[(4-bromophenyl)sulphanylmethyl]-4-[(1,3-dioxo-2,3-dihydro-1H-2-isoindolyl)oxy]butyrate The expected product is obtained using the procedure described in Example 23, Step b, employing as starting material the product described in Example 39, Step a, and with the replacement of phthalimide with N-hydroxyphthalimide.
Step b: tert-Butyl 2-[(4'-chloro-4-biphenyl) sulphanylmethyl]-4-[(1,3-dioxo-2,3-dihydro-1H-2-isoindolyl)oxy]butyrate The expected product is obtained using the procedure described in Example 23, Step a. employing as starting material the product described in the above Step, and using para-chlorophenyltributyltin as reagent.
Step c: 2-[(4'-Chloro-4-biphenyl)sulphanylmethyl]-4-[(1,3-dioxo-2,3-dihydro-1H-2-isoindolyl)oxy]butanoic acid The expected product is obtained in accordance with the procedure described in Example 1, Step i, using as starting material the product obtained in the above Step.

The products of Examples 95 to 99 are obtained in accordance with the procedure described in Example 94, using the appropriate N-hydroxyl compound in Step a and the to appropriate tin compound or boronic acid compound in Step b.

EXAMPLE 95

2-[(4-Biphenyl)sulphanylmethyl]-4-[(1,3-dioxo-2,3-dihydro-1H-pyrrolo[3,4-c]pyridin-2-yl)oxy]butyric acid

EXAMPLE 96

2-[(4-Biphenyl)sulphanylmethyl]-4-[(1,1,3-trioxo-2,3-dihydro-1H-1λ6-benzo[d]isothiazol-2-yl)oxy]butyric acid

EXAMPLE 97

2-[(4'-Chloro-4-biphenyl)methylsulphanylmethyl]-4-[(1,3-dioxo-2,3-dihydro-1H-2-isoindolyl)oxy]butyric acid

EXAMPLE 98

2-{2-[(4'-Chloro-4-biphenyl)ethyl]sulphanylmethyl}-4-[(1,3-dioxo-2,3-dihydro-1H-2-isoindolyl)oxy]-N-hydroxybutyramide

EXAMPLE 99

2-{[4-(3-Pyridyl)phenyl]sulphanylmethyl}-4-[(1,3-dioxo-2,3-dihydro-1H-2-isoindolyl)oxy]-N-hydroxybutyramide The products of Examples 100 to 105 are obtained in accordance with the procedure described in Example 23, using in Step a the compound described in Preparation C and the appropriate tin compound or boronic acid compound, and using in Step b the appropriate N-hydroxyl compound.

EXAMPLE 100

2-[(4-Biphenyl)oxymethyl]-4-(1,3-dioxo-2,3-dihydro-1H-2-isoindolyl)butyric acid

EXAMPLE 101

2-[(4'-Chloro-4-biphenyl)oxymethyl]-N-hydroxy-4-(1,3-dioxo-2,3-dihydro-1H-pyrrolo[3,4-c]pyridin-2-yl)butyramide

EXAMPLE 102

2-[(4'-Chloro-4-biphenyl)oxymethyl]-5-(1,3-dioxo-2,3-dihydro-1H-2-isoindolyl)pentanoic acid

EXAMPLE 103

2-{2-[(4'-Chloro-4-biphenyl)ethyl]oxymethyl}-5-(1,3-dioxo-2,3-dihydro-1H-2-isoindolyl)pentanoic acid

EXAMPLE 104

2-[(4'-Fluoro-4-biphenyl)oxymethyl]-4-(1,1,3-trioxo-2,3-dihydro-1H-1λ6-benzo[d]isothiazol-2-yl)butyric acid

EXAMPLE 105

2-{[4-(3-Pyridyl)phenyl]oxymethyl}-4-(4-oxo-3,4-dihydro-1,2,3-benzotriazin-3-yl)butyric acid The products of Examples 106 to 109 are obtained in accordance with the procedure described in Example 49, with the replacement of phthalimide with the appropriate N-hydroxyl compound in Step a and using the appropriate tin compound in Step b.

EXAMPLE 106

(1R,2S,5R)- and (1S,2R,5S)-2-[2-(4-biphenyl) ethylsulphanyl]-5-[(1,3-dioxo-2,3-dihydro-1H-2-isoindolyl)oxymethyl]-1-cyclopentanecarboxylic acid

EXAMPLE 107

(1S,2R,5) and (1R,2S,5R)-2-[(4-biphenyl) sulphanyl]-5-[(1,3-dioxo -2,3-dihydro-1H-2-pyrrolo[3,4-c]pyridin-2-yl)oxymethyl]-1-cyclopentanecarboxylic acid

EXAMPLE 108

(1R,2S,5R)- and (1S,2R,5S)-2-[(4'-chloro-4-biphenyl)sulphanyl]-5-[(4-oxo-3,4-dihydro-1,2,3-benzotriazin-3-yl)oxymethyl]-1-cyclopentanecarboxylic acid

EXAMPLE 109

(1R,2S,5R)- and (1S,2R,5S)-2-[2-(4'-fluoro-4-biphenyl)ethylsulphanyl]-5-[(4-oxo-3,4-dihydro-1,2,3-benzotriazin-3-yl)oxymethyl]-1-cyclopentanecarboxylic acid

EXAMPLE 110

(1R,2S,5R)- and (1S,2R,5S)-2-[(4-biphenyl)oxy]-5-[(1,3-dioxo-2,3-dihydro-1H-2-isoindolyl) oxymethyl]-1-cyclopentanecarboxylic acid The expected product is obtained in accordance with the procedure described in Example 1, with the replacement of 4-bromothiophenol with 4-bromophenol in Step e, and of potassium phthalimidate with N-hydroxyphthalimide in Step h.

EXAMPLE 111

(1S,2R,5S)- and (1R,2S,5R)-2-[(4'-chloro-4-biphenyl)oxy]-5-[(4oxo-3,4-dihydro-1,2,3-benzotriazin-3-yl)methyl]-1-cyclopentanecarboxylic acid The expected product is obtained in accordance with a process identical to that of Example 10, using 4-bromophenol instead of 4-bromothiophenol.

EXAMPLE 112

(1S,2R,5S)- and (1R,2S,5R)-2-[(4-biphenyl)methoxycarbonyl]-5-[(1,3-dioxo-2,3-dihydro-1H-2-isoindolyl)methyl]-1-cyclopentanecarboxylic acid The expected product is obtained in accordance with the procedure described in Example 20, with the replacement of potassium phthalimidate with N-hydroxyphthalimide in Step c.

EXAMPLE 113

2-[(4-Biphenyl)oxymethyl]-2-hydroxy-5-(4-oxo-3,4-dihydro-1,2,3-triazin-3-yl)pentanoic acid Step a: 2-[(4-Biphenyl)oxymethyl]-5-hydroxy-1-pentene The expected product is obtained in accordance with the procedure described in Example 23, Step a, using as starting material the compound described in Preparation H.

Step b: 2-[(4-Biphenyl)oxymethyl]-5-(4-oxo-3,4-dihydro-1,2,3-triazin-3-yl)-1-pentene A mixture of 13.9 mmol (3.72 g) of the product described in the above Step and 20.85 mmol (3.06 g) of 1,2,3-benzotriazin-4-(3H)-one dissolved in tetrahydrofuran (130 ml) is added dropwise to a solution of 20.85 mmol (5.47 g) of triphenylphosphine and 20.85 mmol (4 ml) of diethyl azodicarboxylate in tetrahydrofuran (80 ml) at 0° C. The resulting mixture is stirred for 1 hour at 0° C. then for 12 hours at ambient temperature. The reaction mixture is concentrated and the expected product is obtained by chromatography of the residue on silica gel using an 85:15 petroleum ether/ethyl acetate mixture as eluant.

Step c: 2-[(4-Biphenyl)oxymethyl]-1,2-dihydroxy-5-(4-oxo-3,4-dihydro-1,2,3-triazin-3-yl)pentane 12.5 mmol (2.4 g, 60% in water) of 4-methylmorpholine N-oxide and then 0.5 mmol (5 ml, 2.5% in 2-methyl-2-propanol) of osmium tetroxide are added to a solution of 10.4 mmol (4.16 g) of the product described in the preceding Step in acetone (50 ml). The reaction mixture is stirred at ambient temperature for 24 hours and then concentrated. The expected product is obtained by chromatography on silica gel using a 1:1 then 2:3 heptane/ethyl acetate gradient as eluant.

Step d: 2-[(4-Biphenyl)oxymethyl]-5-(4-oxo-3,4-dihydro-1,2,3-triazin-3-yl)pentanal A solution of 40.5 mmol (2.9 ml) of dimethyl sulphoxide in dichloromethane (20 ml) is added to a solution, cooled to –60° C., of 23.18 mmol (2 ml) of oxalyl chloride in dichloromethane (50 ml). The reaction mixture is stirred for 15 minutes at –60° C. and then a solution of 11.6 mmol (5 g) of the product described in the above Step in dichloromethane (30 ml) is added dropwise. The reaction mixture is stirred for 30 minutes at –60° C. and then a solution of triethylamine (13 ml) in dichloromethane (20 ml) is added while maintaining the temperature at –60° C. After 15 minutes, the mixture is reheated to ambient temperature and, after 2 hours, hydrolysed with water and extracted with dichloromethane. The organic phases are washed with a dilute hydrochloric acid solution and then with brine and are finally dried with magnesium sulphate. The expected product is obtained by concentration of the organic phase.

Step e: 2-[(4-Biphenyl)oxymethyl]-2-hydroxy-5-(4-oxo-3,4-dihydro-1,2,3-triazin-3-yl)pentanoic acid A solution of 20 mmol (18 g) of sodium chlorite in water (30 ml) is added dropwise to a solution of 10 mmol (4.3 g) of the product described in the preceding Step in dimethyl sulphoxide (10 ml). The reaction mixture is stirred at ambient temperature for 90 minutes and then a solution of 5 mmol (0.685 g) of sodium hydrogen phosphate in water (10 ml) is added. The reaction mixture is extracted with ethyl acetate and the organic phases are washed with brine, dried with magnesium sulphate and concentrated. The expected product is obtained by chromatography of the residue on silica gel using a 9:1 dichloromethane/methanol mixture as eluant.

The compounds of Examples 114 to 121 are obtained in accordance with the procedure described in Example 113, using the appropriate tin compound in Step a and with the replacement of 3H-benzo[1,2,3]triazin-4-one with the appropriate compound in Step b.

EXAMPLE 114

2-[(4'-Chloro-4-biphenyl)oxymethyl]-2-hydroxy-5-(4-oxo-3,4-dihydro-1,2,3-triazin-3-yl)pentanoic acid

EXAMPLE 115

2-[2-(4'-Fluoro-4-biphenyl)ethoxymethyl]-2-hydroxy-5-(4-oxo-3,4-dihydro-1,2,3-triazin-3-yl)pentanoic acid

EXAMPLE 116

2-[(4'-Chloro-4-biphenyl)oxymethyl]-2-hydroxy-4-(1,3-dioxo-2,3-dihydro-1H-2-isoindolyl)butanoic acid

EXAMPLE 117

2-[(4'-Chloro-4-biphenyl)oxymethyl]-2-hydroxy-5-(1,1,3-trioxo-2,3-dihydro-1H-1$\lambda$6-benzo[d]isothiazol-2-yl)pentanoic acid

EXAMPLE 118

2-[(4-Biphenyl)sulphanylmethyl]-2-hydroxy-5-(4-oxo-3,4-dihydro-1,2,3-triazin-3-yl)pentanoic acid

EXAMPLE 119

2-[(4'-Chloro-4-biphenyl)sulphanylmethyl]-2-hydroxy-4-(1,3-dioxo-2,3-dihydro-1H-2-isoindolyl)butanoic acid

EXAMPLE 120

2-[2-(4'-Fluoro-4-biphenyl)ethoxymethyl]-2-hydroxy-5-(4-oxo-3,4-dihydro-1,2,3-triazin-3-yl)pentanoic acid

EXAMPLE 121

2-{[4-(3-Pyridyl)phenyl]sulphanylmethyl}-2-hydroxy-5-(4-oxo-3,4-dihydro-1,2,3-triazin-3-yl)pentanoic acid The compounds of the following Examples are obtained in the same manner, using the appropriate reagents:

EXAMPLE 122

(1R,2S,5R)- and (1S,2R,5S)-2-[2-(4'-chloro-4-biphenyl)ethylsulphanyl]-5-[(1,3-dioxo-1,3-dihydro-2H-benzo[f]isoindol-2-yl)methyl]-1-cyclopentanecarboxylic acid

EXAMPLE 123

(1R,2S,5R)- and (1S,2R,5S)-2-[2-(4'-chloro-4-biphenyl)ethylsulphanyl]-N-hydroxy-5-[(1,3-dioxo-1,3-dihydo-2H-benzo[f]isoindol-2-yl)methyl]-1-cyclopentanecarboxamide

EXAMPLE 124

2-{[2-(4'-Chloro-4-biphenyl)ethyl]sulphanylmethyl}-4-[(1,3-dioxo-1,3-dihydro-2H-benzo[f]isoindol-2-yl)butyric acid

EXAMPLE 125

N-Hydroxy-2-{[2-(4'-chloro-4-biphenyl)ethyl]sulphanylmethyl}-4-[(1,3-dioxo-1,3-dihydro-2H-benzo[f]isoindol-2-yl)]butyramide

EXAMPLE 126

2-[(4'-Chloro-4-biphenyl)methylsulphanylmethyl]-4-[1,3-dioxo-1H-benzo[d,e]isoquinolin-2(3H)-yl]butyric acid

EXAMPLE 127

N-Hydroxy-2-[(4'-chloro-4-biphenyl)methylsulphanylmethyl]-4-[1,3-dioxo-1H-benzo[d,e]isoquinolin-2(3H)-yl butyramide

EXAMPLE 128

2-[(4'-Chloro-4-biphenyl)methoxymethyl]-4-[1,3-dioxo-1H-benzo[d,e]isoquinolin-2(3H)-yl]butyric acid

EXAMPLE 129

2-[(4'-Chloro-4-biphenyl)methoxymethyl]-4-[1,3-dioxo-1H-benzo[d,e]isoquinolin-2(3H)-yl]butyric acid

PHARMACOLOGICAL STUDY OF THE COMPOUNDS OF THE INVENTION

Example A

Enzymatic Inhibition of Metalloproteases

The four recombinant human enzymes used, that is MMP-1 (interstitial collagenase), MMP-2 (gelatinase A), MMP-3 (stromelysin 1) and MMP-9 (gelatinase B), are activated using APMA, 2 mM (4-AminoPhenylMercuric Acetate), at 37° C. for 30 minutes in the case of MMP-2 and MMP-9, and for 1 hour in the case of MMP-1 and MMP-3.

The enzymatic tests are carried out in a 50 mM Tris buffer, 200 mM NaCl, 5 mM $CaCl_2$, 0.1% Brij 35at pH7.7.

Two kinds of peptidomimetic substrates are employed

Dnp-Pro-(β-cyclohexyl)Ala-Gly-Cys(Me)-His-Ala-Lys-(N-Me)Abz-$NH_2$ in the case of the enzymes MMP-1, MMP-2 and MMP-9; this substrate being cleaved between glycine and cysteine to yield a fluorescent derivative (Anal. Biochem., 1993, 212, 58).

(7-methoxycoumarin-4-yl)-Arg-Pro-Lys-Pro-Tyr-Ala-Nva-Trp-met-Lys-(Dnp)-$NH_2$ in the case of the enzyme MMP-3; this substrate being cleaved between alanine and norvaline to yield a fluorescent derivative (Biochemistry, 1992, 31, 12618).

The reactions are carried out in the buffer containing the activated enzyme at a final concentration of 1.25 μg/ml in the case of MMP-1, 2 μg/ml in the case of MMP-2, 1.25 μg/ml in the case of MMP-3 and 1 μg/ml in the case of MMP-9, in the absence and in the presence of the test compound at 5 or 10 different concentrations. The reactions are initiated using 20 μM substrate in a total volume of 100 μl and incubated at 37° C. for 6 hours.

The fluorescence induced after cleavage is then measured using a cytofluorometer fitted with a combination of 340 nm and 440 nm filters for excitation and emission.

Example B

Inhibition of the Formation of Metastases in the Mouse

The anti-tumour activity of the compounds of the invention was studied in the model of B16F10 melanoma grafted by the i.v. route. That tumour exhibits the characteristic of being very invasive and of massively colonising the lungs when it is grafted by the i.v. route. The parameter measured is thus the number of pulmonary metastases.

B16F1O tumour cells are injected by the i.v. route into BDF1 mice on day 1 (1 $10^5$ cells per mouse). The compounds are administered by the i.v. route at 100 mg/kg from day 0 to day 3 (7 animals per experimental group). On day 11, the animals are sacrificed and the pulmonary metastases are counted. The results are expressed as % inhibition compared with the control animals.

Result

The inhibition by the compounds of the invention of the formation of metastases is from 45 to 75%. This is true in particular of the compounds of Examples 49 and 93 of which the inhibition percentages are 73 and 75% respectively.

Example C

Protection of Collagen Matrix Degradation of Articular Cartilage in vitro

The compounds of the invention were studied using a rabbit cartilage collagen matrix degradation model with degradation being induced by IL-1β. The tissue is placed in contact with IL -1β (10 ng/ml) and plasmin (0.1 U/ml) for 2 days. The fraction of OH-proline salted out by the tissue is evaluated by colorimetric measurement (*GRANT R. A. Estimation of OH-proline by the autoanalyzer, J. Clin. Path.* 1964, 17 685). The compounds of the invention were studied after the addition of various concentrations to the culture medium during the two days of the test.

Result

The compounds of the invention appear to have antagonised collagen degradation. The $IC_{50}$ values obtained are of the order of μM. This is true in particular of the compounds of Examples 50 and 93, which exhibit $IC_{50}$ values of 1.0 M and 1.9. μM respectively.

Example D
Pharmaceutical Composition
Formulation for the preparation of 1000 tablets each comprising 10 mg of active ingredient.

| | |
|---|---|
| compound of Example 93 | 10 g |
| hydroxypropylcellulose | 2 g |
| wheat starch | 10 g |
| lactose | 100 g |
| magnesium stearate | 3 g |
| talc | 3 g |

We claim:
1. A compound selected from those of formula (I):

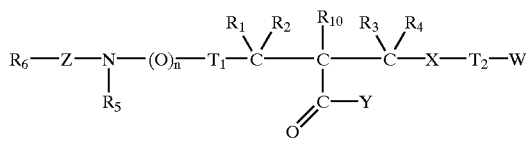

(I)

wherein:
n is 0 or 1,
$R_1$, $R_2$, $R_3$ and $R_4$ independently represent hydrogen or alkyl, or
$R_1$ and $R_3$ form together with the carbon atoms carrying them a $(C_5-C_8)$cycloalkyl and in that case $R_2$ and $R_4$ each represents hydrogen,
$R_5$ and $R_6$ form together with the nitrogen and Z carrying them a saturated, partially unsaturated or unsaturated mono-, bi-, or tri-cyclic group having 5 to 16 ring members and 1 to 7 hetero atoms selected from nitrogen, oxygen and sulphur and/or sulphoxide or sulphone, the cyclic group being optionally substituted by 1 to 7 identical or different substituents selected fro halogen, alkyl, amino, hydroxy, alkoxy, nitro, mercapto, alkylthio, cyano, oxo, imino, thioxo, carboxy, alkoxycarbonyl and aminocarbonyl (optionally substituted on the nitrogen atom by one or two alkyl groups),
$R_{10}$ represents hydrogen or hydroxy, and in the latter case $R_1$, $R_2$, $R_3$ and $R_4$ are independently selected from hydrogen and alkyl,
Z represents —CO— or —SO$_2$—,
Y represents hydroxy, alkoxy, alkenyloxy or benzyloxy or —NH—OR wherein R represents hydrogen or alkyl, alkenyl or benzyl,
X represents: sulphur or —SO— or —SO$_2$— and in those cases $R_3$ and $R_4$ are other than alkyl, or X represents —COO— and in that case $R_1$ and $R_3$ together form $(C_5-C_8)$cycloalkyl, or X represents oxygen,
W represents $W_1$—(A)$_p$ or $W_1$—B—$W_2$—(A)$_p$ wherein $W_1$ and $W_2$ independently represent aryl or heteroaryl, the A substituent of the aromatic cyclic is attached at any of the positions of that cyclic group and represents halogen or alkyl, alkoxy, hydroxy, mercapto, cyano, amino, nitro, cyanoalkyl or thioalkyl, B represents a bond, oxygen or alkylene, alkenylene or alkynylene (wherein any one of the carbon atoms of the alkylene, alkenylene or alkynylene may be replaced by oxygen), and p represents integer of 0 to 5 inclusive,
$T_1$ and $T_2$ independently represent a bond or alkylene, alkenylene or alkynylene, wherein when $T_2$ represents a bond and n is 0 and at the same time $R_1$, $R_2$, $R_3$ and $R_4$ each represents hydrogen, then $R_5$ and $R_6$ form together with nitrogen and the group Z carrying them a bicyclic as defined hereinbefore that is other than 1,3-dioxo-2,3-dihydro-1H-2-isoindolyl, 2,5-pyrrolidinedione or optionally substituted 2,5-dioxo-1-imidazolinyl, its enantiomers, diastereoisomers, and addition salts thereof with a pharmaceutically acceptable acid or base.
2. A compound of claim 1, wherein $R_{10}$ represents hydrogen.
3. A compound of claim 1, wherein $R_{10}$ represents hydroxy.
4. A compound of claim 1, wherein $R_2$ and $R_4$ represent hydrogen.
5. A compound of claim 1, wherein n is 0.
6. A compound of claim 1, wherein n is 1.
7. A compound of claim 1, wherein $R_1$ and $R_3$ form together with the carbon atoms carrying them $(C_5-C_8)$cycloalkyl and $R_2$ and $R_4$ each represents hydrogen.
8. A compound of claim 1, wherein $R_2$ and $R_4$ represent hydrogen and $R_1$ and $R_3$ independently represent hydrogen or alkyl.
9. A compound of claim 1, wherein $R_5$ and $R_6$ form with the nitrogen and the group Z carrying them a saturated, partially unsaturated or unsaturated mono-, bi- or tri-cyclic having 5 to 16 ring members and 1 to 7 hetero atoms selected from nitrogen, oxygen and sulphur and/or sulphoxide or sulphone, the cyclic group being optionally substituted by 1 to 7 identical or different substituents selected from halogen, alkyl, amino, hydroxy, mercapto, alkoxy, nitro, cyano, oxo, imino and thioxo.
10. A compound of claim 1, wherein $T_1$ and $T_2$ are independently selected from bond and alkyl.
11. A compound of claim 1, wherein Y represents hydroxy or —NH—OR—.
12. A compound of claim 1, wherein W represents $W_1$—(A)$_p$ or $W_1$—B—$W_2$—(A)$_p$ wherein p is 1 and B represents a bond.
13. A compound of claim 1, wherein $R_2$, $R_4$ and $R_{10}$ each represents hydrogen, n is 0, $T_1$ and $T_2$ are independently selected from bond and alkylene, W represents $W_1$—(A)$_p$ or $W_1$—B—$W_2$—(A)$_p$ wherein p is 1 and B represents a bond, $R_5$ and $R_6$ form together with the nitrogen and Z carrying them a saturated, partially unsaturated or unsaturated mono- or bi-cyclic group substituted with 1 to 5 hetero atoms selected from nitrogen, oxygen and sulphur and/or sulphoxide or sulphone, the cyclic group being optionally substituted by 1 to 7 identical or different substituents selected from halogen, alkyl, amino, hydroxy, alkoxy, nitro, cyano, oxo, imino and thioxo, and Y represents hydroxy or —NH—OH.
14. A compound of claim 13, wherein $R_1$ and $R_3$ form together with the carbon atoms carrying them $(C_5-C_8)$cycloalkyl.
15. A compound of claim 13, wherein $R_1$ and $R_3$ each represents hydrogen.
16. A method for treating a living animal body afflicted with a condition selected from rheumatoid arthritis, arthrosis, and metastatic cancers, comprising the step of administering to the living animal body an amount of a compound of claim 1 which is effective for alleviation of the condition.
17. A pharmaceutical composition useful for the treatment of a condition selected from rheumatoid arthritis, arthrosis, and metastatic cancers, comprising as active principle an effective amount of a compound as claimed in claim 1, together with one or more pharmaceutically-acceptable excipients or vehicles.

* * * * *